United States Patent [19]

Siguel

[11] Patent Number: 5,075,101
[45] Date of Patent: Dec. 24, 1991

[54] METHOD FOR DIAGNOSIS OF FATTY ACID OR LIPID ABNORMALITIES

[76] Inventor: Edward N. Siguel, P.O. Box 5, Brookline, Mass. 02146-0001

[21] Appl. No.: 507,659

[22] Filed: Apr. 10, 1990

[51] Int. Cl.[5] .................... G01N 31/00; A61K 31/20
[52] U.S. Cl. .......................................... 424/9; 424/2; 514/558; 514/814; 514/824
[58] Field of Search ............... 424/9, 2; 514/558, 814, 514/824

[56] References Cited

U.S. PATENT DOCUMENTS

| | | | |
|---|---|---|---|
| 4,108,603 | 8/1978 | Regnier | 23/230 B |
| 4,297,338 | 10/1981 | Makari | 424/9 |
| 4,338,811 | 7/1982 | Miyagi et al. | 73/23.1 |
| 4,499,186 | 2/1985 | Teodorescu | 435/23 |
| 4,500,964 | 2/1985 | Nickle | 364/300 |
| 4,863,873 | 9/1989 | Matson | 436/63 |

OTHER PUBLICATIONS

Siguel, E. N. et al, Clinical Chemistry, 33:1869–1873 (1987).
Siguel, E. N., Nutritional Support Services, 8(9):24 (1988).
Holman, R. T., American J. Clinical Nutrition, 32:2390–2399 (1979).
Lundberg, Wo, Nutrition Reviews, 38(7):233–5 (1980).
Siguel, E. N., Nutrition and Cancer, 4(4):285–9 (1983).
Siguel, E. N., Arch. Pathol. Lab. Med., 110:792–7 (1986).

Primary Examiner—Glennon H. Hollrah
Assistant Examiner—Gary E. Hollinden

[57] ABSTRACT

A method for measuring more accurately Fatty Acids and Essential Fatty Acid (EFA) Deficiencies (EFAD). The invention includes a disease diagnostic method for the diagnosis of lipid and fatty acid biochemical abnormalities found through the analysis of tissues of a test subject, deriving indices of lipid and fatty acid biochemical status, and analytically comparing patterns or domains obtained from indices of a subject with similar indices derived from tissues of subjects with normal and abnormal biochemistry, for the purposes of diagnosing abnormalities. A specific mixture of nutrients (test mixture), prepared according to this invention, is given to a test subject to modify the tissue composition of said test subject in order to verify or modify a diagnosis, including mixtures of w3 and w6 fatty acids. Another specific mixture of mixture of nutrients (treatment mixture), prepared according to this invention, is given to a test subject to correct lipid and fatty acid abnormalities found in said test subject.

55 Claims, 23 Drawing Sheets

Figure 2

$F_{ci}$ = Concentration of fatty acid i $F_{pi}$ = Percent of fatty acid i $F_{pi} = F_{ci} / $ (Sum of all $F_{ci}$)

Total $wj_c$ = Sum of percents of wj fatty acids (j = 3, 6, 7, 9)

$SAT_p$ = Sum of percents of all saturated fatty acids $EVEN_p$ = Sum of percents of all fatty acids with an even number of carbons $ODD_p$ = Sum of percents of all fatty acids with an odd number of carbons $MONO_p$ = Total $w7_p$ + Total $w9_p$ (fatty acids with one double bond)

$(w7 + w9)_p$ = Total $w7_p$ + Total $w9_p$ (all w7 + w9)

$PFA_p = PFA3_p + PFA6_p + PFA7_p + PFA9_p$ $DFA_p = DFA3_p + DFA6_p + DFA7_p + DFA9_p$ $EFA_p = PFA3_p + PFA6_p$ (essential)

$DEFA_p = DFA3_p + DFA6_p$ (derivatives)

$TRANS_p$ = Sum of percents of all trans fatty acids $LONGCHAIN_p$ = Sum of all fatty acids of chain length $\geq 20$

Variations in the groups listed above

Usual (common) fatty acids = Similar groups but restricted to those fatty acids which are found in healthy subjects in quantities above 0.01%.

Abnormal fatty acids = Similar groups but restricted to those fatty acids which are unusual and rarely found in healthy subjects (the user specifies the meaning of rare and usual).

Similar groups using concentrations instead of percents.

Similar groups using concentrations adjusted by the total fatty acid concentration.

Figure 3

Indices of deficiency or insufficiency of EFA

T/T = 20:3w9/20:4w6      16:1w7 / 18:2w6

$EFA_p$ / $MONO_p$      ($EFA_p$ - $TRANS_p$) / $MONO_p$ $16:1w7_p$ / $20:3w9_p$      $ODD_p$ / $EVEN_p$

Miscellaneous indices

Platelet Aggregation index = 20:5w3/20:4w6

Indices of metabolic activity

DFAi/ PFAi, for i = w3, w6, w7, w9

$F_{pi}$ / $F_{pj}$, the ratio of any two fatty acids. This is primarily used when one fatty acid follows or precedes another in a biochemical pathway

Indices of relative deficiency of w3 vs w6

(DFA3/PFA3)/(DFA6/PFA6)      Total w3 / Total w6

18:3w3 / 18:2w6 = PFA3/ PFA6      DFA3 / DFA6

Similar ratios using concentrations and/or the concentrations adjusted by the regression on total fatty acid concentration.

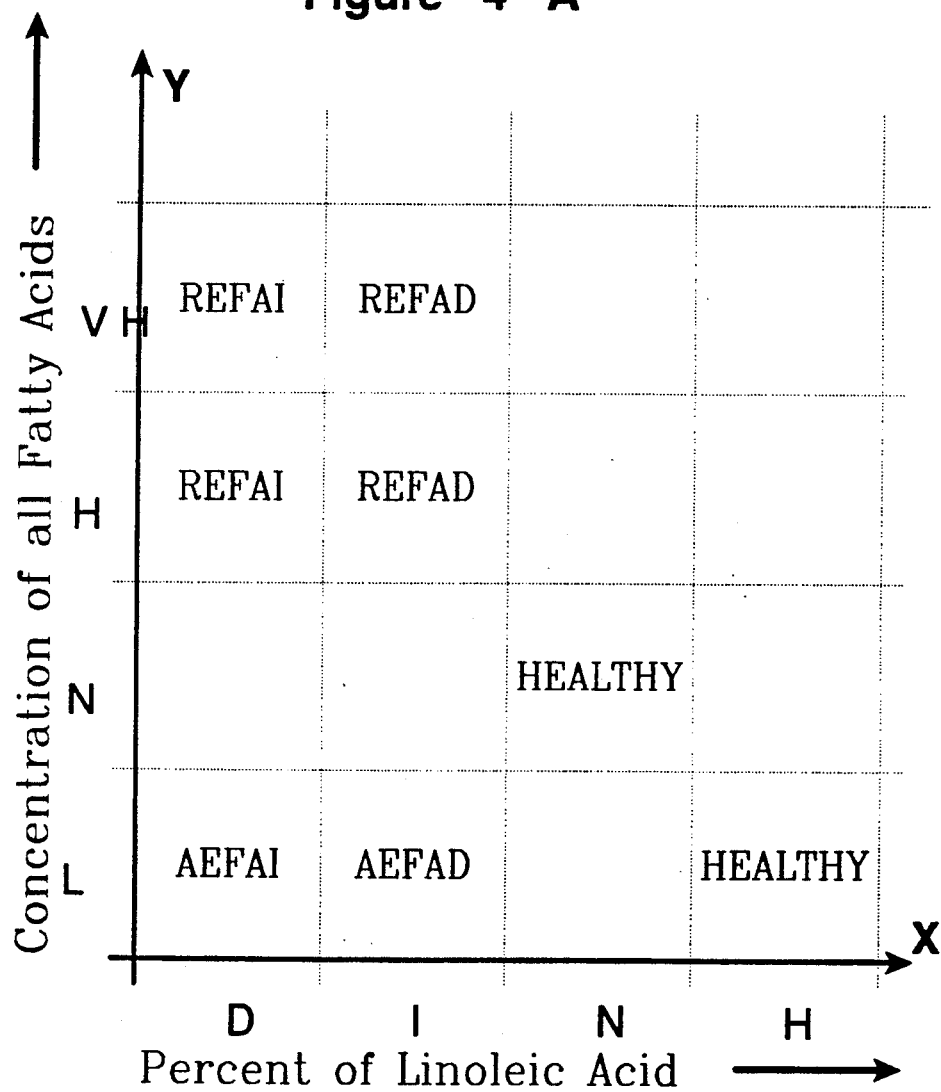

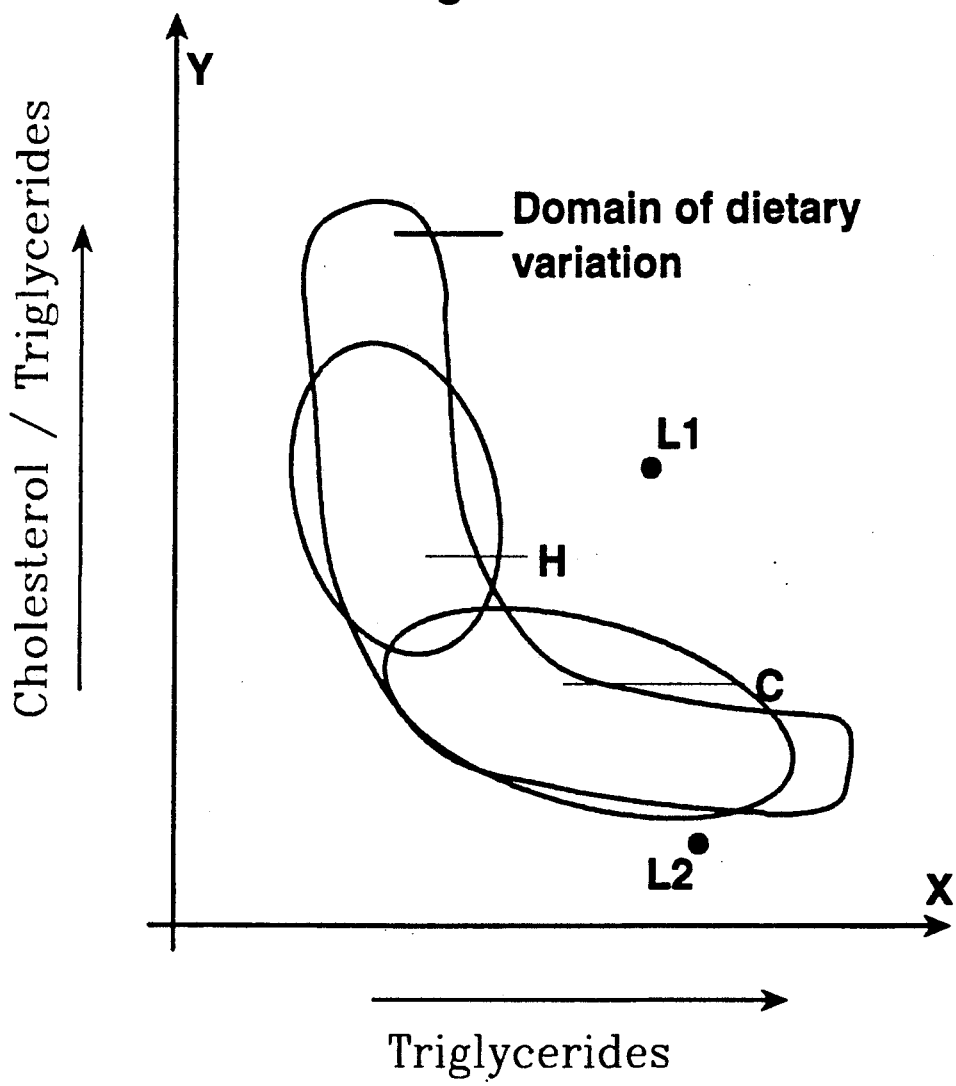

METHOD FOR DIAGNOSIS OF FATTY ACID OR LIPID ABNORMALITIES

BACKGROUND OF THE INVENTION

1. Field of the Invention

This invention relates to a method for diagnosing an abnormal fatty acid (or abnormal lipid) biochemistry or metabolism, by analyzing substances contained in body tissues, and processing the quantities of each substance to compare them with similar quantities obtained from healthy and diseased subjects, and thus produce a diagnosis which may be used to modify the chemical composition of a test subject.

2. Major Nutrients

The major nutrients, i.e., foods that people eat, are fats (lipids), carbohydrates, proteins, vitamins, minerals, water and fiber. The three major types of fatty acids, key components of fat, which are critical for animal health, are: saturated, monounsaturated and polyunsaturated. Other types include: isomers, trans, and branch fatty acids. In contrast to vitamins and minerals, where one can easily obtain the required amounts by taking a few pills (and the body usually destroys or excretes the excess), fatty acids are macronutrients: eating too much leads to overweight; eating too little leads to deficiencies; eating the wrong mixture produces biochemical imbalance and disease. A "substance" is a molecule found in humans, usually a nutrient or a component of a nutrient, or something formed from a nutrient. Carbohydrates, glucose (components of carbohydrates), fats, fatty acids, phospholipids, and fatty acids in phospholipids are examples of substances.

Types of Fat: Saturated, Mono and Polyunsaturated

There are four families of unsaturated fatty acids which are distinct insofar as interconversions between families do not occur in humans. The enzymes for the elongation and desaturation reactions by which the parent (or precursor) fatty acid (PFA) is converted to daughter (or derivative) fatty acids (DFA) within each family appear to be shared by all four families. The rates of elongation and desaturation (formation of double bonds) differ among families and the rank of the families by order of decreasing desaturation rates is $w3 > w6 > w9 > w7$. The term w3 or w6 refers to fatty acids member of the families derived from linolenic (18:3w3) or linoleic (18:2w6) acid, respectively. The w3 and w6 fatty acids are also known as omega-3 and omega-6. The letter "w" stands for the greek symbol "omega".

Each family of unsaturated fatty acids is referred to either by the name of the PFA (oleic, palmitoleic, linoleic, and linolenic) or by the position of the common double bond (w9, w7, w6, and w3, respectively). In the "omega" ("w") nomenclature, oleic acid, the parent of the w9 family, is symbolized by 18:1w9 which indicates it is 18 carbons long and has 1 double bond in the 9th position from the terminal carbon. Likewise, palmitoleic acid is named 16:1w7. These two fatty acids are considered non-essential fatty acids since humans can synthesize them from saturated fatty acid precursors. The other two PFA, linoleic (18:2w6) and alphalinolenic (18:3w3), are known as the essential fatty acids (EFA). Linoleic acid and alphalinolenic acid (hereinafter called linolenic acid) can only be obtained from the diet. This is not true, however, of other types of fatty acids, because humans can convert carbohydrate and protein to saturated and monounsaturated fatty acids. One important consequence of this is that the type of fat humans eat is a major determinant of the type of fat stored by the body.

The four parent (precursor) fatty acids are referred to as PFAi (i=3,6,7,9, for the w3, w6, w7 and w9 families) and their elongation and desaturation products will be referred to collectively as daughters (derivatives), abbreviated DFAi (i=3,6,7,9). There are many derivatives of the EFA, but for simplification all members of the same family will be referred to as one. The symbolic chemical equation is:

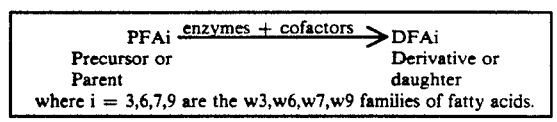

PFA=Precursor fatty acids. DFA=Derivative fatty acids. EFA=Essential Fatty Acids. DEFA=Fatty acid Derivatives of the EFA. For example, the term PFA3 refers to linolenic acid (18:3w3), and DFA3 to its derivative fatty acids such as eicosapentaenoic (20:5w3) and docosahexaenoic (22:5w3). Similarly, the term PFA6 refers to linoleic acid (18:2w6) and DFA6 to its derivative fatty acids such as arachidonic acid (20:4w6).

The properties of fatty acid metabolism are: (a) a fatty acid that starts as a member of given unsaturated family remains with that family; (b) different families may share enzymes; (c) fatty acids of one family may affect the biochemistry of other fatty acids; (d) the DFAi/PFAi ratios follow the order $w3 > w6 > w9 > w7$ in the fasting-state plasma.

Most polyunsaturated fat (PUFA) consists of the EFA and their derivatives, DEFA. The basic equations are:

$$PUFA = EFA + DEFA = (PFA3 + PFA6) + (DFA3 + DFA6)$$

$$PUFA = (PFA3 + DFA3) + (PFA6 + DFA6) = \text{Total } w3 + \text{Total } w6$$

where:
EFA=PFA3+PFA6=Essential Fatty Acids
DEFA=DFA3+DFA6=Derivatives of Essential Fatty Acids Some PUFA consists of derivatives of the w9 and w7 fatty acids, but they are rarely found in humans and their total amount is far smaller than the other fatty acids. When researchers and physicians refer to PUFA they should refer to any of the w3 and w6 families; most physicians apparently are unaware of the differences between w3, w6, w7 and w9. Polyunsaturated fatty acids are really different kinds of fats with different chemical compositions and different medical significance. To simplify discussion in this patent they have been grouped into parents and daughters (or precursor and derivatives). This means that all the daughters (derivatives) can be formed from the parent (precursor). The opposite is usually not true. Each family has one parent and many daughters or derivatives. In total there are four groups: parent and daughter omega-3, and parent daughter omega-6. Table 1 presents where each is found.

TABLE 1

| | Polyunsaturated Families | |
|---|---|---|
| FAMILY | PARENT (PFA) | DAUGHTERS (DFA) |
| w3 | Linolenic (PFA3) | 20:5w3, 22:6w3, and others |
| w6 | Linoleic (PFA6) | 20:3w6, 20:4w6 (Arachidonic), and others |
| Found in | Vegetables | Animals (mostly w6), Fish (mostly w3). |

PRIOR ART

Essential Fatty Acid Insufficiency (EFAI) and Deficiency (EFAD)

A long-prevailing belief has been that the human body's need for essential fatty acids (EFA) is met when tissue levels are sufficient to prevent acute signs of EFA deficiency (EFAD) due to very low levels of EFA. The term EFA Insufficiency (EFAI) denotes low levels of EFA not low enough to produce the symptoms and signs currently associated with EFAD, such as hair loss, and seborrheic dermatitis, but low enough to produce biochemical abnormalities of EFA metabolism and other clinical conditions.

Modern textbooks of nutrition and medicine consider EFAD to be an extremely rare disorder affecting less than 1/1000 people, usually associated with patients on parenteral alimentation who do not receive lipid supplements. These books do not consider the existence of EFAI. That EFAI may cause diseases other than the rare syndromes associated with severe EFAD became testable recently with the availability of modern gas-liquid chromatography.

Importance of EFA to Human Health

Growth in understanding of the molecular biophysics of membranes has led to an appreciation that fatty acid inbalance or insufficient amounts of EFA may impair numerous membrane-based reactions and transport mechanisms, reduce cell life, alter physiologic processes, and produce suboptimal tissue function. Increased platelet aggregation, atherosclerosis and hyperlipidemia may be among the consequences of insufficient EFA. Moreover, reduced dietary intake of EFA may alter the rates of production of eicosanoids, derivatives of EFAs which have a wide range of physiological effects.

Research conducted by the inventor suggests that EFA levels substantially below the mean in healthy individuals, but not so low as to produce classic signs of EFA deficiency, may affect over 10% of the U.S.A. population, and are associated with disorders such as hypercholesterolemia, cardiovascular disease and malabsorption. It is one purpose of this invention to measure EFAI.

Changes in Fatty Acid Metabolism Associated with a Deficiency of w3 or w6 Fatty Acids Studies have shown that reduced cell levels of the EFA produce the following metabolic changes: (a) the amount of w7 and w9 fatty acids increase, most likely produced from saturated fat; (b) the DFAi/PFAi ratios increase; and (c) Mead acid (20:3w9) increases more than Arachidonic Acid (20:4w6), which may decline. The 20:3w9/20:4w6, trienoic/tetraenoic (T/T) ratio increases and may reach values greater than 1.0. A T/T ratio of 0.2 or more has been suggested by researchers as a criterion for EFAD of the w6 family. Improved chromatographic conditions achieved through this invention lead to greater separation of peaks enabling more specific detection of 20:3w9. The result is that the T/T ratios in healthy individuals are far more smaller than previously reported. This invention states that T/T ratios in the range 0.005 to 0.2 are associated with more subtle pathology than the currently recognized clinical signs of EFAD, and EFA intake and metabolism may be more important in health and disease than hitherto appreciated. The increased sensitivity of measurement due to this invention will allow the early diagnosis of fatty acid abnormalities.

Current diagnosis of EFA deficiency has been limited to comparing fatty acid percents obtained for a subject with ranges obtained from a population of healthy subjects ("normal ranges") and the use of the ratio of two fatty acids, 20:3w9/20:4w6 (called the T/T ratio—see above). For example, if a subject has an elevated T/T (over 0.2) this subject is said to be EFA deficient, meaning whole body EFA deficient. M. Roesner and J. P. Grant wrote "Intravenous Lipid Emulsions", published in "Nutrition in Clinical Practice", Vol 2, Issue 3, pps. 96-107. June, 1987. On p.96. they stated that a T/T "ratio greater than 0.4 in tissue and plasma phospholipids has been used to diagnose " EFAD. This approach measures primarily w6 deficiency, and does not evaluate the relative effects of an w3 vs w6 deficiency, or deficiencies of PFA vs DFA.

Relative Versus Absolute Insufficiency of EFA

The inventor has defined a distinction between Absolute EFA deficiency (AEFAD) or Insufficiency (AEFAI) and Relative EFA deficiency (REFAD) or Insufficiency (REFAI). AEFAD describes a condition of low levels of total body stores of EFA. The AEFAD is the traditional pattern of total body deficiency of EFA usually found with fat malabsorption in gastrointestinal disease, or produced in experimental animals deprived of EFA in their diet. Using the inventor's terminology, published studies refer to whole body deficiency when they use the term EFAD, which corresponds to the term AEFAD as described herein. The inventor has determined that the traditional concept of EFAD is only applicable to cases of AEFAD. The AEFAI is a new disorder due to a less severe deficiency with different clinical effects and requiring new diagnostic procedures, such as the method described in this invention. REFAI (and REFAD) refers to a new condition where the body has potentially adequate total body stores of the EFA, but individual cells or tissues do not have enough EFA due to biochemical abnormalities, metabolic defects, transport defects, or other factors which interfere with the optimal utilization of the EFA or DEFA. The inventor has determined that human subjects exist with AEFAI, REFAD and REFAI, and has found (unpublished research) that REFAD and REFAI could affect more than 10% of the U.S.A. population and could be one of the leading causes of cardiovascular disease. Measurement of REFAD and REFAI can be done according to this invention.

Chemists measure about 10 lipids and over 50 fatty acids. Methods which separate and quantitate the amount of each fatty acid in a mixture of substances in a given tissue include gas liquid chromatography (GLC), High Pressure Liquid Chromatography (HPLC), Thin Layer Chromatograpy (TLC), Spectrophotometry, and antigen-antibody reactions. These methods quantify each lipid and fatty acid found. Currently, the diagnosis of a lipid and/or fatty acid abnormality is based upon the quantification of specific lipids and specific fatty acids using well known separation methods such as those mentioned above. The lipids commonly measured are cholesterol, triglycerides, phospholipids, the cholesterol inside lipoproteins such as High Density Cholesterol (HDL cholesterol), and various derivatives of the above lipids, such as cholesterol esters.

These quantifications are limited to diagnosing an abnormality affecting only the specific measured lipid or fatty acids. They do not diagnose complex biochemical abnormalities of production or transport of essential fatty acids or their derivatives. For example, current diagnosis measures the plasma quantity of linoleic acid to determine if there is a deficiency of linoleic acid, but will not identify an abnormality of linoleic acid metabolism that produces normal levels of plasma linoleic acid but abnormal derivatives or utilization of that linoleic acid.

In addition, when the normal ranges are too broad due to insufficient accuracy, people with abnormalities may be diagnosed as being normal. This happens when the techniques to measure fatty acids do not allow accurate detection of fatty acids present in small quantities (under 1% of total measured fatty acids).

Recent Advances in GLC

Until recently, most published studies failed to distinguish cis- from trans- fatty acid isomers, and the chromatogram peaks for biochemically significant fatty acids such as 20:3w9 were superimposed on those of other compounds. Many important fatty acids, including linolenic acid, eicosapentaenoic acid (20:5w3), and mead (20:3w9), are present in very small quantities and elute very close (with most chromatography columns) to other fatty acids leading to large measurement errors. Using recently developed capillary columns and taking great care to eliminate sources of contamination and to optimize chromatographic conditions for fatty acid methyl esters (FAME), the inventor has achieved substantially better separations than hitherto published studies. This improved separation enables much better quantitation and identification of peaks which in turn permits more and better indicators of fatty acid abnormalities to be developed. These new indicators permit enhanced detection of abnormal fatty acid metabolism. One significant feature of the published and unpublished research is that new separation technology allows the measurement and identification of fatty acids previously not measurable.

Disease Diagnosis

Many disease diagnostic apparatus, such as X-Ray machines and biochemical analyzers, provide a multitude of measurement results which must be combined to obtain a disease diagnosis. For example, the patterns produced by an X-Ray machine are analyzed by a CAT scanner to provide a pattern which diagnoses a tumor. The novelty in a CAT scanner is not the production of X-Rays or X-Ray pictures, but the integration of thousands of X-Rays to produce a two or three dimensional pattern that is used to diagnose disease.

Thousands of substances are contained in body tissues, and over 100 fatty acids and lipids are present in body tissues. Separation methods which quantify the presence of a substance can determine the quantity of hundreds of substances. However, it is humanly impossible to utilize so many substances for the determination of a disease without a process to interpret them and arrive at a diagnosis. For example, all the X-Ray measurements of a CAT scan, by themselves, would be useless without the process that translates them into a disease diagnostic tool.

Methods for diagnosing a disease by analyzing the amounts of certain substances in the body have been described in various scientific papers and patents. For example, A. B. Robinson and L. Pauling in a paper entitled "Techniques of Orthomolecular Diagnosis" in "Clinical Chemistry", Vol. 20, No. 8, 1974, pp. 961-965, reported a pattern recognition technique to analyze amines and amino acids. U.S. Pat. No. 4,338,811 to H. Miyagi et al. discloses a disease diagnostic method and apparatus in which pattern diagrams formed from peak areas (measures of quantities of a substance) and retention times (identity of a substance) are used to compare healthy and abnormal subjects. Miyagi is similar to the instant invention in that both describe a process to analyze quantitites of substances and reach a diagnosis. However, in Miyagi the peaks of each substance are used without any further changes. On the other hand, the instant invention takes quantitites measured by any instrument, calculates concentrations and/or percents, and processes them further to create variables whose values are called "indices". The set of all indices for one subject is called his characteristic pattern or characteristic index. The set of all characteristic patterns for a group of similar subjects is called a domain. The disease of a test subject (such as a patient) is determined, according to the instant invention, by comparing said subject characteristic pattern with the domains of the healthy and disease subjects.

Miyagi forms a specific pattern using only one measure of the quantity of each substance. The instant invention takes other measures of the quantities of each substance (percents and/or concentrations), processes them further to produce other objects (indices), and then analyzes them in a specific manner to reach a diagnosis of an abnormality of fatty acid or lipid biochemistry or metabolism. The current invention does not use retention times.

U.S. Pat. No. 4,500,964 to A. F. Nickle discloses a method for diagnosing errors in data entry systems. Nickle does not refer to any particular apparatus and makes no claims regarding the origin of the data. Data is keyed into a data entry system and, through a series of formulas, it is compared with previously specified data sets to determine if the data is in error or is correct. A data base of error messages alerts to the nature of the error. Nickle refers to error bits, error masks, and error messages. The present invention does not deal with errors in keying data but compares one set of data with other sets for purposes of diagnosing an abnormality. Although Nickle and the present invention are similar in that both disclose a process of comparison, they are different in the data used, the comparisons made, the purposes of the comparison and the result of the comparison.

U.S. Pat. No. 4,499,186 to M. C. Teodorescu et al. discloses a method to diagnose autoimmune diseases by analyzing the immune response under specific circunstances. The present invention analyzes concentration of nutrients or lipids rather than immune responses.

U.S. Pat. No. 4,297,338 to J. G. Makari discloses a method whereby an antigenic product is injected into a subject and the response of the subject is measured in order to diagnose immunity to malignant tumors. In the present invention subjects are fed (orally or through other means) mixtures of fatty acids and other nutrients to measure the response of the subject and diagnose an abnormality of fatty acids. U.S. Pat. No. 4,108,603 to F. E. Regnier compares one dimensional profiles of hemoglobin for normal and abnormal subjects. The present invention compares multidimensional profiles using concentrations of nutrients or lipids rather than hemoglobin.

Current diagnosis of lipid abnormalities merely classifies a patient according to the results of lipid measurements. A patient is said to have high cholesterol, low HDL, high triglycerides, etc. The diagnosis does not provide an indication of the cause of the abnormality. Moreover, the diagnosis using lipids is not tied to using fatty acids. The current invention displays lipid patterns associated with dietary variations and permits the identification of patterns associated with disease or genetic abnormalities.

Fatty acids are not currently used for diagnosis except for some very rare disorders. Because of competition among fatty acids for enzymes, an abnormality of one fatty acid could lead to insufficient formation of derivatives of essential fatty acids and have adverse effects on health. Because of metabolic competition, an abnormality of one fatty acid leads to an abnormality of another. Merely measuring all fatty acids without analyzing their interaction may lead to misleading diagnosis. Therefore, the degree of competition among substrates and the relative rates of the desaturation/elongation reactions need to be measured to diagnose abnormal fatty acid biochemistry and to determine how the fatty acid composition of the diet influences cellular lipid metabolism. The present invention provides a means to characterize the biochemistry of fatty acids and its relationship to the biochemistry of other nutrients.

Many people have high blood pressure, high cholesterol and cardiovascular disease of unknown origin. The instant invention diagnoses if there is a fatty acid abnormality and determines the nutritional treatment to follow.

Deficiencies of vitamins or minerals involve microdeficiencies which can easily be treated with a daily pill. Abnormalities of fatty acids involve deficiencies of some fatty acids (usually w3 and w6) and excesses of other fatty acids (usually saturated fats). Moreover, the balance of w3 and w6 is critical. Humans need to eat macroquantities of fat (grams), but too much fat leads to overweight. To optimize the body composition of fat one must know the nature of the abnormality and develop a carefully tailored diet. Too much or too little of specific fats may fail to improve the health of the patient, and in fact may cause other problems, such as an abnormality of prostaglandins, a major hormone. The treatment diet often requires a substantial modification over previous eating patterns. Therefore, it is critical that the fatty acid abnormality be properly diagnosed. Most people require diets high in PFA3 and/or PFA6 and/or DFA3 and/or DFA6. The optimal mixture of these fatty acids (in the diet) can be determined by the application of this invention.

It is impossible to predict, from dietary records and questions, the amounts of each fatty acid that a person has been eating over his lifetime. There are too many factors that affect dietary intake of polyunsaturated fats, including the type of food, the nature of food processing (cooking, storage, etc.), and the supplements one takes. Food processing alters the polyunsaturated fat. For example, margarines, although made from polyunsaturated fat, are high in trans polyunsaturates that alter the metabolism of the cis polyunsaturates. The instant invention measures not only biochemical composition but the interaction of all fatty acids and lipids and detects biochemical alterations caused by fatty acid interaction.

People often have a combination of diseases, some mild, some more severe. Traditional unidimensional diagnosis, i.e., looking at one variable at a time or a combination of variables without taking into account variable interactions, may diagnose the most significant disease but may fail to recognize the significance of coexisting disorders. Multidimensional analysis opens the door to more comprehensive evaluation by looking at whole metabolic pathways rather than individual variables at a time.

A person who absorbs fat poorly needs a very special diet, perhaps intravenous supplements. Intravenous supplements are expensive and risky; therefore they are used only when there is certainty that a person cannot absorb fat and needs essential fatty acids. Current interest in supplementing the diet with fish oils rich in DFA3 is likely to produce excessive body tissue levels of DFA3 and lead to abnormal lipid metabolism and possible bleeding and anemia. It is then important to diagnose the cause to properly modify the diet.

Conversely, some people may indeed have low body levels of DFA3 and need to take supplements, and the question is: should they eat more PFA3 or more DFA3?. The very active conversion of PFA3 to DFA3 suggests that vegetarians who follow a diet rich in PFA3 and practically devoid of DFA3 (found in fish) may not need to change their diets. On the other hand, elderly people have been suspected of having relatively less active fatty acid enzyme pathways, so supplementation of their diets with DFA3 may be necessary for optimal health. This invention explains how to diagnose abnormalities of DFA3.

SUMMARY OF THE INVENTION

This invention provides a novel method for early and effective diagnosis and detection of biochemical abnormalities of lipid and fatty acids in subjects including humans, animals and plants. It also explains how such abnormalities can be treated with specific mixtures of different types of fats.

This invention differs from traditional diagnostic procedures whereby the diagnosis is based on the values of one or more substances and those values, considered as normal or abnormal, are defined independently from each other for each one of such substances (referred to as one-dimensional ranges). For example, it is traditional in medicine to prepare a "profile" which consists of the values of N variables. For each such variable, the profile presents the values of a test subject and a range of values considered "normal" for each individual substance. The range of values for one substance does not depend on the range of "normal" values for another substance. A physician looks at the results and determines what substances (values) are within or outside the "normal" ranges. Thus, a certain number of variables are "normal" and the rest are "abnormal". Similarly, one may have ten different chest X-rays. Such groups of X-rays are different from a chest CAT scan which presents an integrated view of the chest. In this invention, the "normal" or "abnormal" ranges are defined by considering simultaneously two or more substances.

This invention uses indices derived from instrument measurements of substance concentrations (or percents) to compute a domain or pattern or diagram that characterizes each disease. The pattern is used to characterize an abnormality; it can also be used to diagnose the disease and may also be used to prescribe optimal treatment.

The invention starts with measures of the concentrations and/or percents of substances found in samples of tissues (including blood) and processes them to derive a set of characteristic indices. Said characteristic indices may be multidimensional points or representations in multidimensional spaces. A domain or pattern is formed from a set of characteristic indices for a group of similar subjects. Domains are formed for sets of healthy subjects and sets of subjects with diseases and stored in computer-readable formats. Domains may be multidimensional closed volumes in multidimensional spaces. The characteristic indices of a test subject are compared with the domains of healthy and diseased subjects to diagnose an abnormality. After the diagnosis is made, the test subject is given a mixture of nutrients which modify his body composition and biochemistry. This serves to confirm or revise the diagnosis, and to determine what nutrients must be given to the test subject to correct the diagnosed abnormality.

For example, the quantity (concentration) of each type of fatty acid present in plasma is measured using Gas Liquid Chromatography. Processing those quantities the invention calculates variables including the percent of each fatty acid as a percent of the sum of all fatty acids identified, sums of selected groups of fatty acids including the total amount of Essential Fatty Acids EFA, and ratios of groups. The values of said variables are displayed in a multidimensional space that separates subjects into groups or domains according to the nature of the biochemical abnormality. The invention diagnoses a deficiency or excess of a specific set of fatty acids, or a specific metabolic abnormality that alters the biochemistry of fatty acids (including an enzymatic block that inhibits the formation of some fatty acids). These results are used to determine how much of each fatty acid or other nutrients like Vitamin E, a subject must eat or avoid to correct the deficiency or abnormality.

A subject, either because of his diet (i.e., being vegetarian), age, disease, nutritional deficiency, genetics, drugs or other factor, may require supplements of PFAi, DFAi, other nutrients such as Zinc, or any combination. This invention helps determine what nutrient combination is most effective in making his characteristic pattern closer to the healthy domain. A user prepares a nutrient mixture (either as a dietary supplement or as a complete new diet). The subject tries it for several weeks. The user measures the characteristic pattern again to determine whether the changes are in the right direction. Differences between the old and the new characteristic pattern provide clues to modify the diet. They also assist to prepare a treatment diet.

OBJECTS AND ADVANTAGES

Accordingly, it is an object of the present invention to provide a comprehensive method to diagnose fatty acids and lipid abnormalities.

It is another object of the present invention to provide a method for using combinations of concentrations and percents of fatty acids to improve disease diagnosis.

It is still another object of the present invention to identify more than one disease concurrently, and the relative contribution of each disease to the diagnosed biochemical abnormality.

It is still another object of the present invention to verify a diagnosis by feeding a test diet or test mixture of specific nutrients prepared according to this invention.

It is still another object of the present invention to treat a patient by feeding a diet or test mixture of specific nutrients prepared according to this invention.

It is still another object to measure more accurately small quantities of fatty acids, including the ratio of 20:3w9/20:4w6, which has been reported to be 0.2 in normals. Said method will show that normals have levels below 0.02, and therefore the difference between normals and diseased subjects is enhanced and early deficiencies may be better diagnosed.

Various advantages and features of novelty which characterize the invention are pointed out with particularity in the claims annexed hereto and forming a part hereof. However, for a better understanding of the invention, its advantages and objectives obtained by its use, reference should be had to the drawings which form a further part hereof and to the accompanying descriptive matter in which there is illustrated and described preferred embodiments of the invention.

BRIEF DESCRIPTION OF THE DRAWINGS

FIG. 2 lists selected variables and groups of fatty acids used in this embodiment.

FIG. 3 lists Ratios and Ratios of Ratios of fatty acids used in this embodiment.

FIG. 9A is a diagram of an embodiment of the apparatus of this invention.

FIG. 9B is a flowchart of a computer program that implements an embodiment of the apparatus of this invention.

REFERENCE NUMERALS AND LETTERS IN THE DRAWINGS

Figure 1:
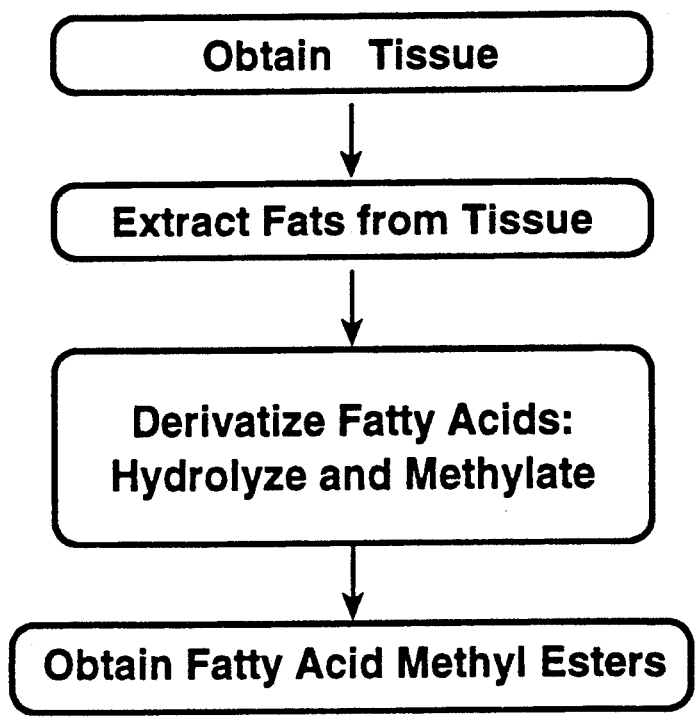
FIG. 1A presents a chemistry flow chart from one preferred embodiment of the disease diagnostic method according to the present invention.
FIG. 1B presents a chromatography flow chart thereof.
FIG. 1C presents a multidimensional pattern, points and domains flow chart thereof.
FIG. 1D presents a disease diagnosis and probability chart thereof.
FIG. 1E presents a chart illustrating updating of a diagnosis by using a test mixture of nutrients.
FIG. 1F presents a chart illustrating treatment with a mixture of nutrients.
FIG. 1G presents a chart illustrating updating multidimensional characteristic indices and modifying treatment.
FIG. 1H presents a chart illustrating updating the treatment mixture after measuring the effects of treatment.
Figure 1:
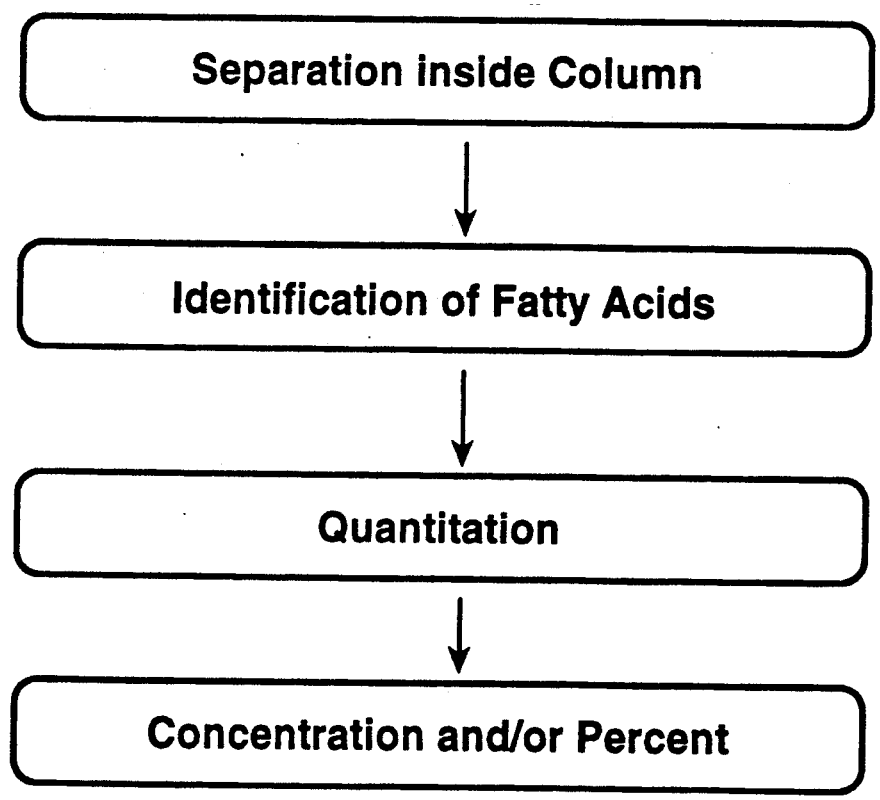
Figure 1:
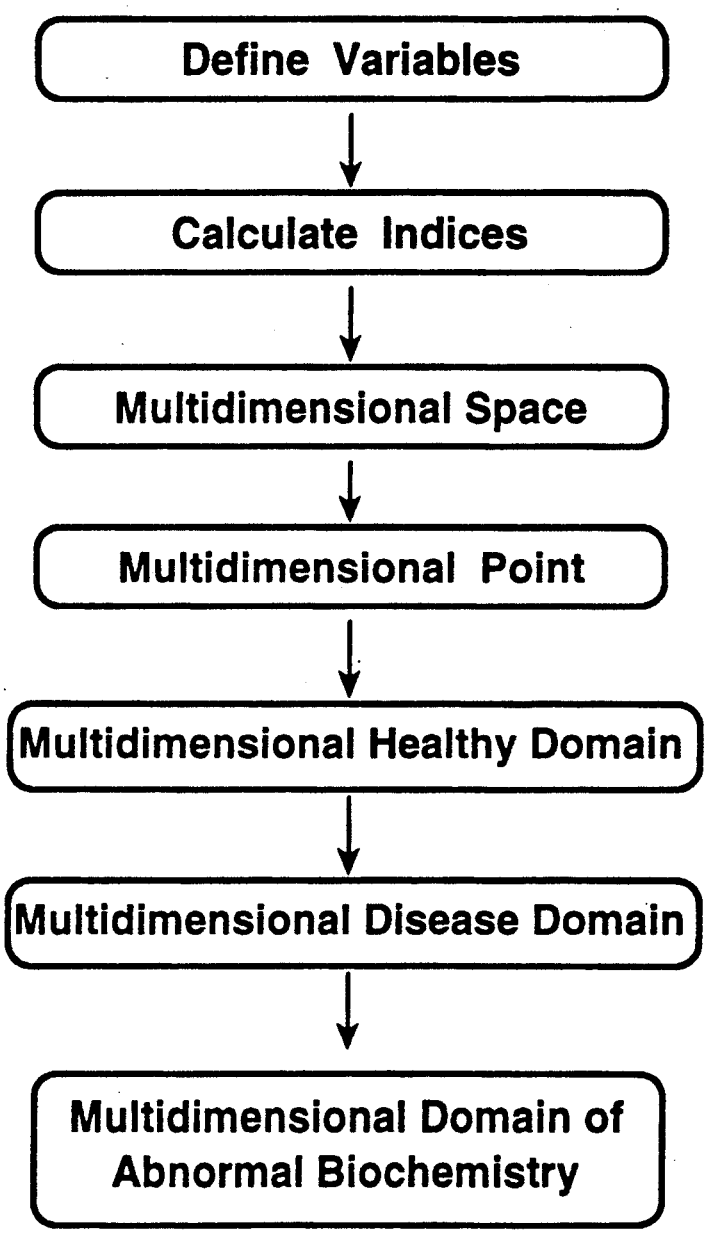
Figure 1:
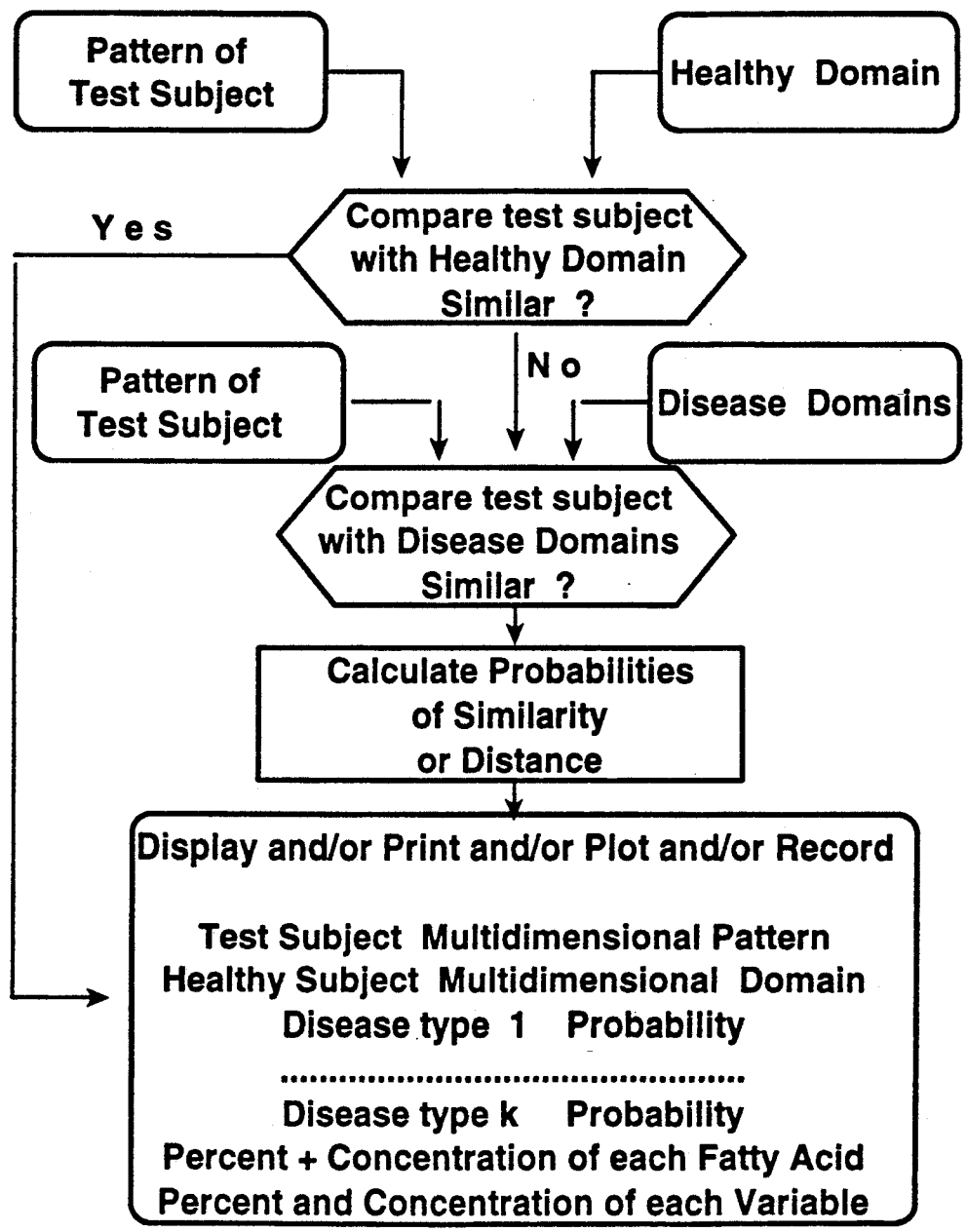
Figure 1:
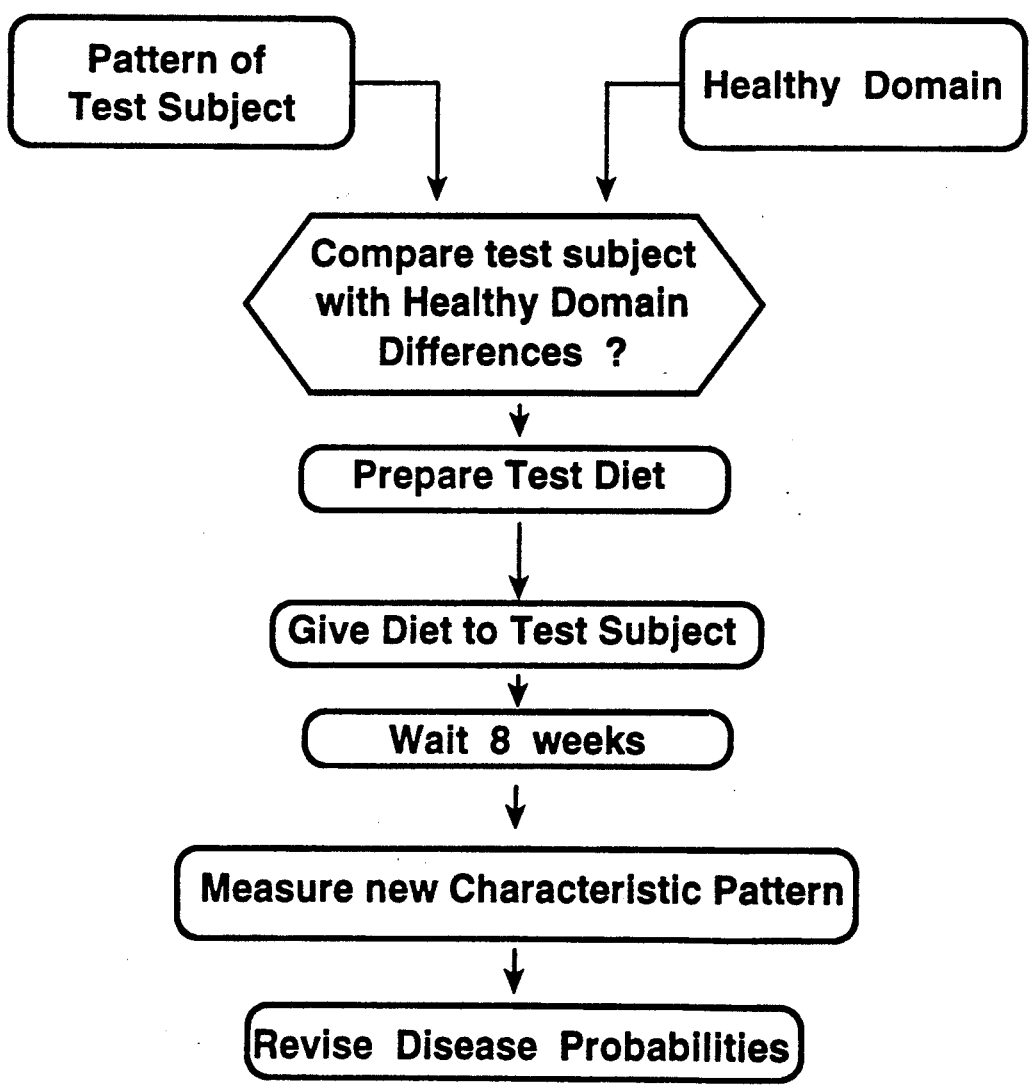
Figure 1:
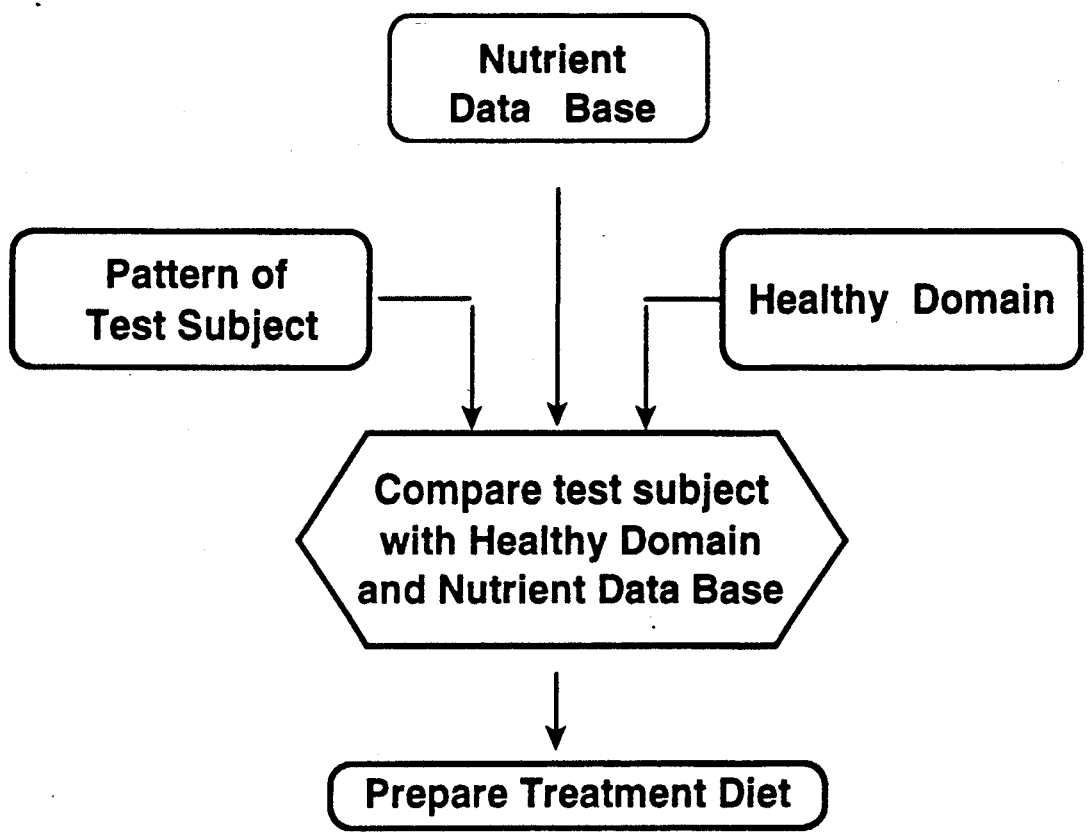
Figure 1:
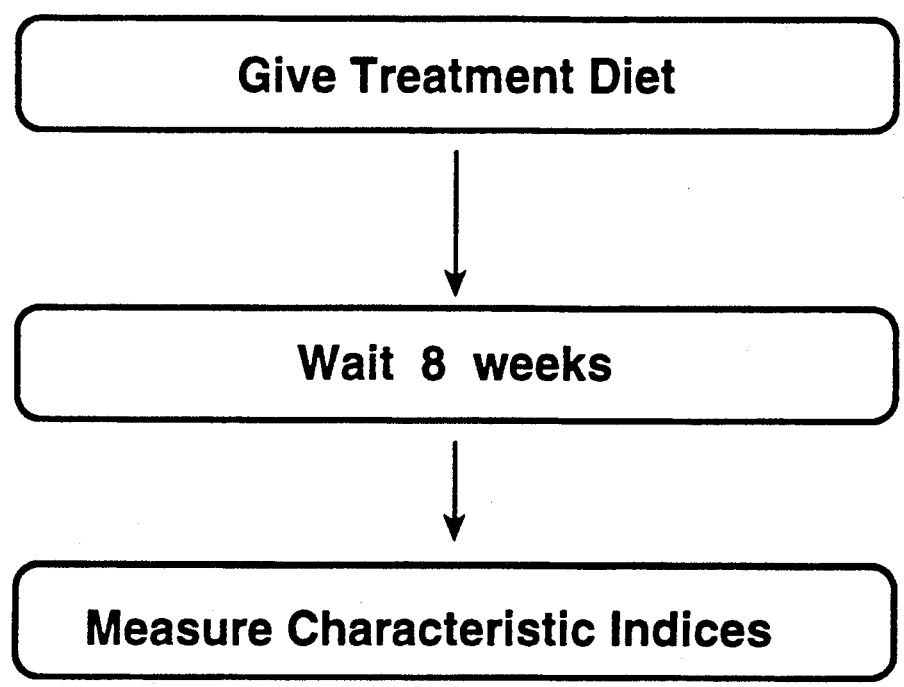
Figure 1:
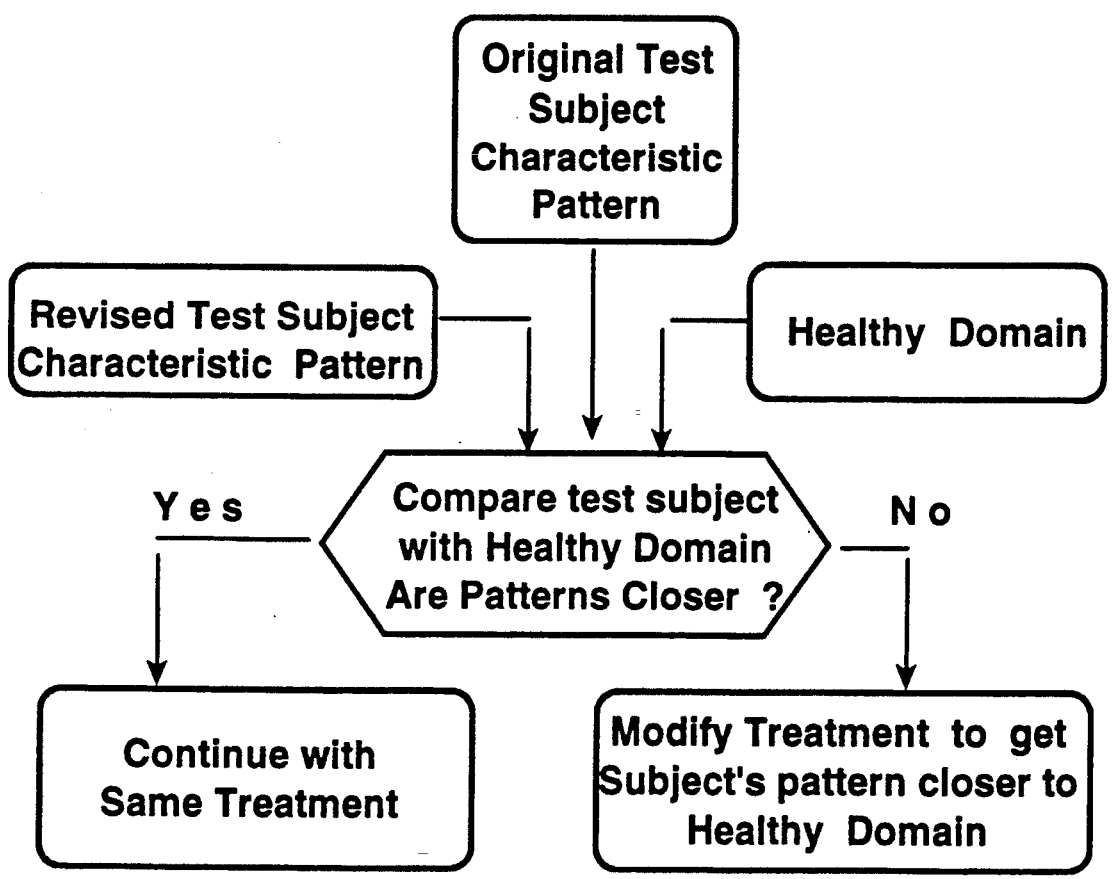

N=Healthy or Normal Subject.
P1=Patient #1. Normal subject with borderline characteristics.
P2=Patient #2. Normal subject with borderline characteristics.
P3=Patient #3. Patient with AEFAI.
P4=Patient #4. Patient with REFAI.
P5=Patient #5. Patient with w3 REFAI.
P6=Patient #6. Patient with DFA3 REFAI and partial metabolic block.
P6'=Patient #6 after a therapeutic diagnostic test with a diet high in EFA.
P7=Patient #7. Patient with excessive levels of DFA3 and bleeding.
L1, L2=Patients with lipid abnormalities, most likely not caused primarily by bad eating (dietary variation). The cause is likely to be a genetic abnormality.
M1, M2=Subjects with disorders of monounsaturated fatty acids.
S=Subjects with Severe EFA Deficiency
C=Subjects with Coronary Artery Disease.
G=Subjects with Gastrointestinal Disease and fat malabsorption.
L=Subjects with Lipid abnormalities.
H=Healthy or normal subjects.

Symbols on Axes

D=Deficient; I=Insufficient; N=Normal; H=High; L=Low; VH=Very High.

DETAILED DESCRIPTION OF THE INVENTION AND PREFERRED EMBODIMENTS

Two separate sets of enbodiments are described: one presents an enhanced method to measure 20:3w9/20:4w6 and small fatty acids; the other specific approaches for diagnosis and treatment.

Embodiment of the Method to Accurately Measure Fatty Acids and 20:3w9/20:4w6 ("T/T")

This embodiment of the invention measures T/T at levels below those previously reported, leading to reduced T/T levels for healthy subjects. Another purpose is to more accurately measure small peaks. The present invention is based on the idea that using extraordinary steps to prevent impurities, together with better separation and integration, small peaks (less than 1% of total identified fatty acids) can be measured with far more accuracy than previously reported.

The key issues are to obtain a high signal to noise ratio and separate fatty acids well, particularly 20:3w9 from other fatty acids. For that purpose, the analytical process must be as clean as possible to minimize interference with undesirable substances. The procedures used to analyze fatty acids have been described before by the inventor and others. Holman et al. stated that T/T above 0.2 is indicative of EFA deficiency (See Holman R. T., Smythe L., Johnson S.: "Effect of sex and age on fatty acid composition of human serum lipids", Am J Clin Nutr 32:2390-2399, 1979 and Lundberg WO: "The significance of cis, cis, cis 5,8,11 eicosatrienoic acid essential fatty acid deficiency". Nutr Rev 38:233-235, 1980). The inventor proposed that it was possible to measure T/T more accurately and such measurement would lead to far lower normal levels. In experiments conducted by the present inventor and reported in order to obtain further subjects to study, the present inventor has shown that the mean of a reference population of apparently normal subjects was 0.01 to 0.02. Levels above 0.02 were considered abnormal. See Siguel E.N., Blumberg J. B., Caesar J. "Monitoring the Optimal Infusion of Intravenous Lipids: Detection of Essential Fatty Acid Deficiency". Archives of Pathology and Laboratory Medicine. 110: 792-797, 1986.; Siguel, E. N., Chee, K. M., Gong J., Schaefer, E. J. "Criteria for Essential Fatty Acid Deficiency in Plasma as assessed by Capillary Column Gas-Liquid Chromatography". Clin Chem 33:1869-1873, 1987; Siguel E. N. Nutrient Charts: "Essential Fatty Acids". Nutr. Support Services, Vol 8, No 9, September, 1988.

During those experiments the inventor found that existing instrumentation, even after modifications by the inventor, was unable to detect levels of T/T below 0.005-0.01 due to the small signal to noise ratio. The inventor has since tried additional steps and has found that the combination of steps described below produce a higher signal to noise ratio leading to far smaller levels of 20:3w9/20:4w6 in healthy humans than previously reported. Depending on the diagnostic purpose, levels above 0.005, 0.01, 0.015 or 0.02 are considered abnormal.

For the purposes of this example, it is presumed that fatty acids are extracted from tissue using any of published reports and methylated to form fatty acid methyl esters (FAME). The FAME are injected into a Gas Liquid Chromatograph (GLC), separated with a capillary column and detected with a Flame Ionization (FID) detector (see Slover T., Lanza E.: "Quantitative analysis of food fatty acids by capillary GC". J Am Oil Chem Society 56(12): 933-943, 1979).

Fatty acid analysis involves three major steps: 1) preparation of FAME; 2) Separation of FAME with GLC (using H or He as carrier, and Air+H for the FID flame); 3) Integration of FAME peaks.

FAME Preparation

Using any available procedure to prepare FAME, the following additional steps are done:

(1) Use only glass or Teflon or stainless steel for all items that come in contact with the sample of the chemicals used. This includes repipettors, tubes, vials, septa, screw caps, etc. Moreover, it is often necessary to cover tubes and/or vials with Teflon tape before placing the top because fumes from the chemicals may touch the plastic or rubber or other material in the top and bring contaminants back into the sample or the chemicals used.

(2) Personnel must wear clean gloves without powder to prevent the hand from contaminating the sample, and a face mask is required to prevent contamination from saliva.

(3) All chemicals used must be of the highest purity available, suitable for GLC. This includes chemicals labeled for GLC or "pesticide Grade" or very high purity.

(4) Whenever possible, use only disposable clean items, such as tubes and vials.

(5) All materials used, such as tubes, vials and pipettors, must be rinsed with solvents before use. Solvents include Chloroform and Methanol. One approach is to place them in a clean glass container with the solvent and magnets, and place the container on a magnetic stirrer. Alternatively, they may be placed on a container inside an ultrasonic cleaner. To dry them, they should rest, inverted, on stainless steel or Teflon or Glass. If the tubes and other parts rest on plastic racks, or paper, or wood, they may become contaminated with fumes and must be cleaned again or discarded.

(6) Use small quantities of material. For plasma, use about 100 microliters and inject less than 1 microgram of fatty acids. Using less quantities means that peaks are smaller and better separated.

Chromatography Separation (1) Use Swagelok fittings and Copper tubing for all gas connectors (stainless steel or teflon is also acceptable). Clean all tubing and connectors with Chloroform, and/or Methanol, and/or Acetone and/or Methylene Chloride. If commercially available, obtain the necessary valves and connectors without any lubricant. If they have lubricant, it must be cleaned to avoid contaminating the gases.

(2) Use Pressure Regulators of the highest purity available. For this embodiment, High Purity Regulators with Stainless Steel diaphragm are adequate. The regulators must be cleaned with vacuum and solvents (Chloroform and Methanol for this embodiment). No rubber/plastic parts.

(3) Gases. Use gases of the highest purity available.

(4) Filters. Use filters (also known as gas purifiers) of the highest purifying capacity available. Use filters that clean excess water, carbon molecules and other impurities from the carrier gases and the detector gases. The carrier gas must be filtered to remove $O_2$. Use several types of commercial filters available to remove gas impurities. In addition, use particle filters to remove undesirable particles. Use filter size of 0.002 mm. Said filters can be found in the catalogs of companies that sell chromatographic supplies, such as SUPELCO. Clean all connectors with solvents (Chloroform and Methanol for this embodiment).

(5) Use the longest available capillary column which is designed specifically to separate FAME. A 50 m is used for this embodiment. A precolumn or similar technique is used to prevent column contamination.

(6) The detector and injector must be cleaned as often as necessary to maintain very small noise levels. This requires the use of low bleed septa and equivalent parts for the GLC. Temperatures and flow conditions for the injector and detector are experimented until optimum measures of peak areas are determined.

(7) The criteria for cleanliness of all procedures can be determined by injecting a blank extract, that is a tube with no sample that has been analyzed as if it were a sample. The injection from such a tube should produce no significant peaks other than the solvent used for the injection.

(8) For this embodiment, use an oven temperature programming method that starts at 80° C. and increases to 220° C. at 1° per minute. Methods are tried sequentially until the best separation is achieved. The procedure to do so requires skill in identifying the optimal separation which requires the least total chromatographic time. The approach is to start first with constant temperatures at 150° C. Then, according to the results, reduce the temperature for the earlier peaks and increase it for later peaks (through trial and error) until all the peaks observed are separated. After all the peaks are separated, a further run is made at a slower rate of change of temperature to verify that none of the peaks split when the separation proceeds more slowly. If they do, then repeat the process again. Once all the peaks are separated, look at time intervals where no peaks appear and try to increase the temperature faster to reduce the run time while maintaining peak separation. This approach often produces a run length longer than previously used by other researchers.

(9) Use the lowest possible attenuation to maximize output signal while preventing the highest peak from overloading the detector.

Integration

The integrating system should display the beginning and end of each peak, and the baseline, on a CRT screen where it can be determined whether the peak was properly integrated. The integrating system should allow for reintegration of improperly integrated peaks. Most integrators improperly calculate the baseline for small peaks, which then requires manual reintegration, a process not feasible without a visual display of the actual peak and its baseline. This approach eliminates all integrators commonly used and requires a computer-based system for chromatography (several are available commercially). Use a low attenuation so that the baseline fluctuation can be easily visualized. For this embodiment, the baseline noise should be at least $\frac{1}{4}$" in height. This allows accurate placement of the beginning and end of each peak. Most researchers use a high attenuation leading to flat baselines which make it impossible to determine if the peak was correctly integrated. The use of a low attenuation and a display where the baseline noise fluctuations are large and clearly seen is another difference with chromatograms currently reported in technical publications.

One purpose of this invention is to get a high signal to noise ratio by maintaining the cleanest possible environment in all the steps of analyzing fatty acids. What is new in the present invention is that the inventor cleans almost everything with solvents, including new clean disposable glassware. Not only plastic is avoided, but also the contact of fumes from solvents with plastic or materials other than glass, metal or teflon. A chromatographic method is used to separate all fatty acids even if such a method requires a very long analysis time. Most people prefer to lose some separation in exchange for a faster analysis time. The electronic display of the signal (on a monitor) shows the noise fluctuations enlarged, allowing incorrectly integrated peaks to be correctly reintegrated.

Consequences

Previously published studies mentioned above indicated that the 20:3w9/20:4w6 ("T/T") ratio of healthy humans is about 0.2 to 0.4. With the procedures described above, the 20:3w9 peak becomes separated from closely found peaks such as 20:2w6 and 20:3w6 and 20:3w7, and it is measured with higher accuracy. The inventor found that healthy humans have a mean T/T around 0.01, with a minimum detectable T/T around 0.005. With the improvements according to this invention, the minimum detectable T/T is below 0.005. It is a consequence of the present invention that such lower T/T can be measured.

Application

The invention indicates that such reduced level of T/T can be used as a diagnostic tool applicable to a large segment of the population. Medical textbooks indicate that EFA deficiency is extremely rare and diagnosis of EFA deficiency is essentially limited to those very rare cases, probably less than 1/1000 of the U.S.A. population (fewer than 100 cases are reported in scientific journals). For that reason, tests for diagnosis of EFA abnormalities are not routinely done in the U.S.A., and the inventor has not found a commercial clinical laboratory that analyzes patterns of fatty acids in humans. The present invention states that EFA deficiency is a common disorder, affecting at least 1% (probably over 10%) of the U.S.A. population—10 to 100 times more!. The reason is that most individuals with cardiovascular disease and/or hypertension have T/T between 0.01 and 0.03; individuals with hyperlipidemia or hypercholesterolemia (between 30% to 70% of the U.S.A. population, according to the criteria used) have T/T in a similar range. When the lowest detectable T/T is around 0.01 and the mean is around 0.02, most deficiencies of EFA are undetected, in part due to measurement error. Shifting the accuracy of T/T so that the lowest detectable is around 0.002-0.005, and reducing the normal range, would mean that deficiencies of EFA become detectable in a large segment of the U.S.A. population.

For example, consider a radar gun used by the police that can only measure speeds over 70 mph. Few speeders are detected with said gun. If a new gun measures over 30 mph, then more speeders are found. Similarly, if the lowest measurable cholesterol were 250 mg/dl, almost everyone would have "normal" cholesterol. When the lowest measurable cholesterol is 150, it is found that healthy people have cholesterols below 200 mg/dl, and most people have abnormal cholesterol levels.

Similarly, with the present invention it will be found that many people are defficient in EFA. With the previously described test, deficiencies of EFA were very rare. The significance of the reduction from accurately measuring T/T from 0.02 levels to below 0.01 is that 0.005 to 0.02 delimits the difference between many healthy and deficient subjects. The inventor proposes several upper normal range for humans. Values above 0.02 are indicative of substantial EFAD. Values above 0.015 are indicative of mild EFAD, typical of the average population in the U.S.A. considered in good health (the average american is at high risk of cardiovascular disease). Values above 0.01 are indicative of very mild EFAD, typical of the average young and healthy population in the U.S.A. Values below 0.005 reflect a population in very good health, with low risk of cardiovascular disease. Different values or levels of T/T diagnose different conditions. With the present invention, T/T below 0.02 will be measured accurately, greatly enhancing the ability to detect EFAI and making EFAI a significant disorder rather than merely a theoretical disease without any practical applications. It also detects a deficiency at an early stage, before it can cause substantial body harm.

Using the same approach, other small peaks can be measured more accurately. In particular, peaks such as 16:1w7 and other w7 and w9 peaks become markers of metabolic shifts; 20:5w3 may be measured more accurately leading to better ratios of 20:5w3/20:4w6 which correlate with bleeding times and measure how likely it is for the blood to form clots (coagulability status).

Embodiment of the Diagnosis and Treatment Invention

This invention presents a comprehensive and specific method for the diagnosis of biochemical abnormalities of lipids and fatty acids, similar to the expansion of a conventional X-ray machine into a sophisticated three dimensional CAT scanner.

Referring to the drawings in detail, an embodiment of the disease diagnostic method according to the present invention will be described with reference to the flow chart shown in FIGS. 1A, 1B, 1C, 1D, 1E, 1F, 1G and 1H, as well as to the other Figures.

It is important to recognize that the invention has several separate independent components or modules. The multidimensional representation (FIGS. 1A-1C) is independent of later aspects. The diagnostic part (FIG. 1D) is also independent of later parts. The disease verification (FIG. 1E) is independent of previous or later parts. It could be used with diagnostic procedures different from the ones described in FIG. 1D. The types of treatment (FIGS. 1F, 1G and 1H) are also independent of testing and/or diagnosis. Thus, each component may be used alone or in combination with the other parts. The invention is claimed for each separate component and for all combinations of the components.

Using known procedures, fatty acids are extracted from plasma lipids and analyzed with available instruments to produce a Quantity of Each Fatty Acid. This quantity is a concentration in grams of fatty acid per unit of tissue (alternatively, it could be a percent). Specifically, the methodology as illustrated in FIGS. 1A and 1B is to obtain plasma and/or cells and/or adipose tissue, extract the fat contained therein, and derivatize the substances for separation with a separation instrument. Chemical procedures are used to extract the lipids from tissues, hydrolyze and methylate the fatty acids and prepare fatty acid methyl esters (FAME), following known techniques. Other embodiments could prepare different derivatives of fatty acids, such as ethyl esters or free fatty acids. The FAME are injected in a chromatography column inside a Gas Liquid Chromatograph (GLC) controlled by a computer system. The GLC-computer separates and identifies fatty acids, and produces a report with the quantity of each fatty acid, following techniques described in scientific journals. Other embodiments could use other methods to quantify each substance. The result is a concentration ($F_{ci}$) and/or a percent ($F_{pi}$) for each fatty acid i.

For this example, it is considered that the total cholesterol, total cholesterol esters, and total triglycerides, have been measured according to current technology. The fatty acids identified are the fatty acids found in whole human plasma in concentrations above 0.0005 mg/dl, including the cis fatty acids chain length 12 to 26, and the monounsaturated and polyunsaturated fatty acids of the w3, w6, w7 and w9 families.

From these measurements the variables indicated in FIGS. 2 and 3 are calculated, both for percents and concentrations. Other embodiments measure fatty acids in concentrations above 0.001 mg/dl, 0.005 mg/dl, 0.01 mg/dl, 0.05 mg/dl, 0.1 mg/dl. It is more expensive to measure smaller quantities and, for diagnoses of common conditions, it is sufficient to measure the fatty acids in higher concentrations.

Percents are the amount of a given fatty acid as a percent of the total amount of fatty acids within a specified group. These quantities are combined to produce indices (values) for variables (see FIG. 1C). An index is the value of a variable for a specific subject. A multidimensional space (n-variables) is created by assigning a variable to each axis. For a given subject, the plot of the values of all the indices produces a multidimensional point (pattern). In a multidimensional space it is a point; in another representation, such as a table, it would be a pattern—a pattern is a more general term. This point is called the characteristic pattern or index and represents the fatty acid and lipid composition and biochemistry of a given subject. A domain is formed from the set of all points (patterns) of a given group of subjects. In this embodiment the term domain refers to the smallest closed volume that contains the set of all points of a given subject. The term range is reserved for the normal and abnormal limits on one axis. For example, in two dimensions, the domain may resemble an asymmetrical ellipsoid. In three dimensions, the domain may resemble a distorted ball. The range is a line in one dimension. Other embodiments of domains are the smallest n-dimensional cube, or the smallest close volume that contains 90% of the subjects (to exclude unusual cases).

As illustrated in FIG. 1C, the concentrations and percents are used to create a multidimensional space and a characteristic pattern for each subject. The concentrations $F_{ci}$ of each fatty acid are the values of the variables concentrations. The percents $F_{pi}$, expressed as percentages of the total amount of a group of fatty acids, are the values of the variables percents, i.e., $$F_{pi} = \frac{F_{ci}}{\text{Sum of all the } F_{ci}}$$

where i = a predefined group of fatty acids.

The values of the variables groups, $G_{ck}$ and $G_{pk}$, are formed as follows:

$G_{ck}$ = the sum of the concentrations of fatty acids in a predefined set k of fatty acids.

$G_{pk}$ = the sum of the percents of all fatty acids in a predefined set k of fatty acids.

FIGS. 2 and 3 list some of the groups for this embodiment.

If M represents the total number of variables, the number of possible groups using sums of variables is equal to the sum of all combinations of all variables in groups of size 1 to M. The number of combinations of M fatty acid into groups of size k is $(M!/k!).(M-k)!$. The total number of groups is the sum from k=1 to k=M and it is equal to $2^M - 1$. See W. Feller, "An introduction to probability theory and its applications", Vol 1, 3rd Edition, John Wiley & Sons, Inc., New York, 1968. In this embodiment the variables considered are (in percents and concentrations):

(1) Linoleic acid ($PFA6_p$)
(2) Linolenic acid ($PFA3_p$)
(3) Derivatives of linoleic acid ($DFA6_p$)
(4) Derivatives of linolenic acid ($DFA3_p$)
(5) $20:3w9_p$, that increases when subjects have low EFA levels
(6) $EFA_p = PFA3_p + PFA6_p$; $DEFA_p = DFA3_p + DFA6_p$
(7) $MONO_p$ = sum of all w7+w9 fatty acids (excluding polyunsaturated w7 and w9, which are an insignificant proportion of MONO)

(8) SatFat$_p$ = sum of all saturated fatty acids
(9) C = Total Cholesterol
(10) TG = Total Triglycerides
(11) C/TG
(12) CE = Total cholesterol esters
(13) CE(PFAi) = percent of PFAi in CE; i = 3, 6, 7, 9
(14) HDL/C = The amount of Cholesterol in High Density Lipoproteins divided by the Total Cholesterol
(15) D3/P3 = DFA3/PFA3
(16) D6/P6 = DFA6/PFA6
(17) R$_{3366}$ = (D3/P3)/(D6/P6)
(18) Total fatty acid concentration
(19) Variables similar to variable #13, the percent of PFAi in phospholipids, total triglycerides, and High Density Lipoproteins.
(20) ODD = Sum of fatty acids with an odd number of carbons; EVEN = Sum of fatty acids with an even number of carbons (even chain fatty acids).

Similar variables using the concentrations of the fatty acids instead of the percents, i.e., PFA6$_c$, PFA3$_c$, etc., may also be used. In other embodiments other nutrients are used to compute the G$_k$'s, and the groups may consist of any combination of nutrients, including sums of concentrations and percents.

Variables ratios, R$_{ij}$, and ratios of ratios, RR$_{ijmn}$, which equal R$_{ij}$/R$_{mn}$, are formed as follows:

$R_{ij} = F_{ci}/F_{cj}$, the ratio of any two concentrations $F_{ci}$ and $F_{cj}$.

It may also be the ratio of any two percents, or, more generally, the ratio of any two groups G$_i$ and G$_j$:

$R_{ij} = G_i/G_j$

For example, the ratios DFAi/PFAi are abbreviated Di/Pi, where i = 3, 6, 7, 9); and therefore:

$(D_i/P_i)/(D_j/P_j) = R_{iijj}$ and
$(DFA_3/PFA_3)/(DFA_6/PFA_6) = R_{3366}$

A two dimensional domain is obtained by plotting on the X axis one of the indices named before, against a Y-axis measuring concentrations of fatty acids. The example in FIG. 4 uses X = F$_{pi}$ where F$_{pi}$ = percent of linoleic acid, and Y = FA$_c$ where FA$_c$ = Concentration of all fatty acids. These two values are chosen because they represent two aspects of fatty acid deficiency: percents to measure relative deficiencies, and concentrations to measure absolute deficiencies. On the X-axis four areas are marked: Deficient (D), Insufficient (I), Normal (N), High (H). On the Y-Axis four areas are marked: Low (L), Normal (N), High (H), Very High (VH). These four areas delineate hypothetical rectangular domains, based on hypothesized biochemical pathways or biochemical values, where subjects may fall. Other regions represent other medical conditions.

FIG. 4A displays said theoretical metabolic domains representing Relative and Absolute Essential Fatty Acid Deficiency and Insufficiency. The X-axis consists of percent of linoleic acid; the percent variable reflects the Relative Deficiency. The Y-axis consists of levels of total plasma fatty acid concentration (similar to total lipid concentration); the concentration variable reflects the Absolute Deficiency. Hypothetical Subjects with REFAD, REFAI, AEFAD and AEFAI are marked in FIG. 4A.

For this embodiment of the invention, the lipids and fatty acids have been measured in the following groups of healthy and disease subjects: (a) a healthy group, labeled "H"; (b) a group of subjects with Coronary Artery Disease, labeled "C"; (c) a group of subjects with Gastrointestinal Disease leading to malabsorption, labeled "G"; (d) a group of subjects with severe malabsorption, labeled "S"; and (e) a group of subjects with very high plasma lipids, i.e., with very high levels of cholesterol and/or triglycerides, labeled "L".

Group H are subjects without any known disease, in good physical and mental health. They have average levels of plasma lipids and plasma fatty acid concentrations (called "normal") and average to high percent of EFA in plasma. Group C are patients who have been in treatment because they have symptoms of coronary artery disease. Group G are patients with fat malabsorption problems. They can eat orally but are thin and have been eating special diets high in saturated fat, such as Medium Chain Triglycerides. Depending on the nature of their diet and disease, these subjects will have varying levels of EFA, and generally low total fat in their body and low plasma fatty acid concentrations. Group S are patients with severe fat malabsorption problems. They cannot obtain enough nutrients by mouth and must be fed parenterally (intravenously) and had been fed in this way for over one year but have not received intravenous lipids. These subjects are thin and have low amounts of fat stored in adipose tissue, and moreover the fat stored has very small quantities of essential fatty acids (EFA). They have low total plasma fatty acid concentration, and very low percent of the EFA. Group L patients have very high plasma total cholesterol and/or total triglycerides. They include subjects with values far above the ranges expected to be found when the only cause is a bad diet, and therefore they are suspected of having genetic abnormalities or a disease that affects lipids, such as diabetes or thyroid disease.

As may be most clearly seen in FIG. 5A, for each group of subjects the percent of linoleic acid is plotted on the X-axis and the concentration of all fatty acids on the Y-axis. The closed curves delineate the domain (areas) containing the 2-dimensional points for each group of subjects. These are empirical domains, to be distinguished from the one-dimensional domains (i.e., ranges) A, I, N, H (High), VH (Very High), and two-dimensional domains REFAD, REFAI, AEFAD, AEFAI based on the hypothesized biochemical characteristics illustrated in FIG. 4A.

FIG. 5B displays the subjects in relation to the domains of FIG. 5A.

Heretofore, to establish reference levels for clinical parameters, scientists computed the mean and standard distribution of the results of a given parameter, such as cholesterol, using a group of healthy subjects. From those results a reference range is computed, usually the mean plus or minus one or two standard deviations. When the results of a given subject fall outside the reference range, the subject is said to have an abnormal test result. Measuring two variables it is possible to prepare a rectangular reference range, although traditionally scientists do not use multidimensional representations of test results. The use of multidimensional (greater than 1) domains is a significant difference with current diagnosis technology. Traditional one dimensional plots or diagrams such as the one in the Miyagi patent fail to properly diagnose fatty acid abnormalities. The rectangles in FIG. 6A are formed with two conventional diagnostic ranges (one for each axis) represented in two dimensions. In this particular example, the two variables are percent of linoleic acid and concentration of total fatty acids, and the limits of the rectangles are the mean plus or minus the standard deviation of the variable for each group of subjects (which includes approximately 95% of the observations). However, even this technique shows ranges for healthy and disease subjects different from the corresponding irregular domains that enclose actual measurements as shown in FIG. 5A. These irregular domains are the smallest space that includes all the observations, or a certain percent, such as 95% of the observations. For comparison purposes, FIG. 6B shows the subjects in the context of the domains of FIG. 6A, and FIG. 6C combines FIGS. 5B and 6B.

Diagnoses begins after the domains are established as shown in FIG. 1C. Using the chemistry and chromatography methodology of FIGS. 1A and 1B, a multidimensional index for an individual to be tested is established. The index of the test subject is then plotted against the domains as shown in FIGS. 4B, 5B and 6B. The initial disease diagnosis is determined by the distances between the characteristic pattern of said test subject and each domain. The multidimensional point (characteristic index) for a specific test subject is compared with the healthy domain. If the point is inside the healthy domain, the test subject is considered to have normal fatty acid and lipid biochemistry. If it is outside the healthy domain, further analysis is done as follows.

Multidimensional distances are calculated between each of the domains (healthy and disease-specific) and the multidimensional point for said test subject. Let $D_k$ be the distance of said test subject to disease domain k. These distances can be computed using a variety of well known measures of distances used in multivariate discriminant analysis or equivalent techniques. For this example, using the two dimensions of FIG. 5B, distances are calculated as the geometric distance between the geometric center of the area of each domain and the two-dimensional point representing said test subject. A similar approach may be used in M-dimensions. A disease probability is calculated that represents the proximity of said test subject to each disease domain. For this embodiment, the probability of disease k is inversely proportional to $D_k$:

Probability of Disease $k = A[(1/D_k)/(\text{Sum of all } 1/D_k \text{ for all } k)]$ where A = adjustment constant The distances to each of the disease and the healthy domains and the probability that the subject has a given disease is then displayed and recorded. The result is a display of the most likely diagnosis using measures of similarity and distance. It also indicates which indices (individual variables) are within the healthy domain and which ones are outside, representing abnormalities that need to be corrected.

FIG. 1D summarizes the diagnostic process. The pattern of a test subject is compared with a healthy domain. If similar, said subject is considered healthy. Otherwise, the pattern of said test subject is compared with disease domains. Probabilities of similarity or distance are calculated and used to identify disease probabilities.

To verify the first or initial diagnosis of FIG. 1D, a test mixture (test diet) of substances containing fatty acids is prepared and used to supplement or replace usual meals and produce a change in the characteristic pattern, thereby verifying the diagnosis. This procedure is described in FIG. 1E. For this embodiment, the mixture (diet) contains an amount of each fatty acid proportional to the difference between said test subject characteristic point and the healthy domain mean point, restricted to four groups of fatty acids: (a) linoleic; (b) linolenic; (c) total saturated; (d) monounsaturated fat. This restriction considers the EFA (precursors) and all the other major types of fat and makes it easy to prepare a test mixture or diet. The subject eats the test mixture or diet for 8 weeks and is retested (of course, the user may specify the diet and the period of time to wait prior to retesting). A new characteristic point is measured and used to revise or confirm the diagnosis (disease probabilities). If the diagnosis was correct, the new distance Dk between the new point and the healthy domain should be smaller than the original distance (see examples below). If the diagnosis was incorrect or incomplete, a new test mixture is prepared and the above steps are repeated.

An example of a test diet calculation for this embodiment is as follows. Table 2 below indicates the amount of each type of fatty acid in a test subject's plasma (his characteristic pattern), and the corresponding means of the healthy domain. The difference (healthy-test subject) is the Test Diet.

TABLE 2

| Test Diet for Diagnostic Purposes | | | | |
|---|---|---|---|---|
| | Percent of each type of fatty acid | | | |
| Domains | w3 | w6 | MONO | SatFat |
| Healthy Mean | 6 | 50 | 29 | 15 |
| Test subject | 3 | 40 | 27 | 30 |
| Resulting Test Diet | 3 | 10 | 2 | −15 |
| Actual Test Diet | 3 | 10 | 2 | 0 |

Because it is not possible to eat a negative amount of food, the diet will consist of w3, w6 and MONO in the proportions of 3:10:2. This translates to the percents of 3/15, 10/15 and 2/15, respectively. In this test diet, all w3 is linolenic acid (PFA3) and all w6 is linoleic acid (PFA6). To follow this mixture the test subject must eliminate practically all saturated fat from the diet. Most dietitians know how to prepare a diet with these specifications.

Notice that the first or initial diagnosis tested with this invention may have been arrived by means other than the ones presented in this invention. If the subject is closer to the healthy domain after the test diet, the initial diagnosis was correct.

Assuming the diagnosis is correct, a treatment mixture (treatment diet) of fatty acids is prepared following a similar procedure. FIG. 1F illustrates the process. The pattern of a test subject is compared with the healthy domain. From a nutrient data base a treatment diet is prepared to bring the test subject pattern closer to the healthy domain.

Treatment or test diets are easily achieved by restricting saturated fat and calories and adding one to two tablespoons of a mixture of soybean (high in w3 and w6) and corn or safflower oil (high in w6). Alternatively, a data base with the fatty acid composition of nutrients is used to prepare foods that meet the specified requirements for each fatty acid. The treatment diet may require derivatives of the EFA if the subject has a metabolic block. The subject is retested at a later time. If the test mixture or new diet has moved his index closer to the healthy domain, he is continued on the same mixture. Otherwise, a new mixture (treatment diet) is prepared using the results of his new characteristic pattern. A similar procedure may be used with a diagnosis arrived through a different mechanism.

After the subject is given the treatment mixture he is retested (FIG. 1F and 1H). If said test subject pattern is closer to the healthy domain, he continues with the same treatment mixture. Otherwise, a new treatment mixture is prepared as previously indicated.

Applications of this Embodiment

The following cases are illustrations of applications of this embodiment of the invention.

Patients P1-P7 arrive for diagnosis. For each patient all the variables are measured and the multidimensional points are formed as indicated above. Of course, many facts have been simplified for these illustrations. FIGS. 4B, and 5B have been prepared for the most significant domains. The invention diagnoses disease as follows.

P1, P2 and N. Examples of Healthy Subjects and a Subject with Mild Disease

FIGS. 4B and 5B presents several diagrams with the location of subjects P1, P2 and N. In FIG. 4B, points P1, P2 and N represent, respectively, the characteristic indices of patients P1, P2 and N. Because N is inside the healthy subject domain, N is considered a healthy or "Normal" subject. Patient P1 is diagnosed as not healthy, most similar to a G patient; patient P2 is diagnosed as healthy.

Notice that a patient may fall into more than one domain. The user has the option of deciding what domains to consider for a particular diagnosis. Subject P2 is close to group C and the domain of REFAI (see FIGS. 4B, 5B). Therefore, he is also considered to be borderline REFAI, and not as healthy as subject N which is further away from the REFAI domain.

P3. Example of Subject with AEFAI

Ms. P3 is a thin woman that complains of diarrhea and abdominal pain for many months. The physician wants to know: a) Is the diarrhea severe?; b) Does it cause fat malabsorption?; c) Is it a severe problem?; d) Should the patient eat a different fat mixture?. Using whole plasma, the results show that P3 has very low levels of the percent of linolenic acid, very low levels of $FA_c$ and high levels of the percent of 20:3w9. Her two-dimensional point is shown in FIG. 5B. Because she is closest to the G group, she is classified as having fat malabsorption probably due to gastrointestinal disease. Adipose tissue analysis (not shown) proves that she has very little fat, and very little storage reserves of EFA. This patient is diagnosed as having malabsorption that interferes with her ability to obtain (absorb) EFA. To further verify the diagnosis, Ms. P3 is asked to eat two tablespoons of soybean oil (rich in EFA) for 8 weeks and to return for further diagnosis. When she returns, she states that the oil produces severe diarrhea. The new multidimensional point is about the same as before. The physician now feeds her lipids intravenously and finds that her multidimensional point moves closer to the healthy domain. Diagnosis: fat malabsorption. Most likely she will require occassional intravenous feeding of EFA, with a ratio of w3/w6 calculated from the distances between her values and the healthy domain values.

If the new multidimensional point after the oral diet high in EFA (soybean oil supplemented) was within the domain of the healthy subjects, she would have been diagnosed as a person who ate poorly and ate very few EFA, perhaps having the disease of anorexia nerviosa (these are subjects who eat very unbalanced diets, often deficient in EFA, and are very thin, but misrepresent their eating habits).

P4. Example of Subject with REFAI

Mr. P4 is a 45 year old white male, 5"8", 185 lbs (overweight), with cholesterol of 250 (high), triglycerides of 180 (high), Blood pressure 130/90 (mildly elevated), who complains of occassional shortness of breath when exercising, but otherwise considered to be in good shape.

The analysis show that he has elevated $FA_c$ (as expected, because of his elevated lipids), a percent of EFA within the Insufficient range, a percent of SatFat above the normal range, a mildly elevated 20:3w9. His characteristic pattern is closest to the C domain and is also similar to the domains of subjects with REFAI and with deficiencies of both w3 and w6 (these domains are not shown), but a relatively larger deficiency of w3 than w6. To move his point inside the healthy domain he needs to eat a mixture of w3 and w6 but more w3 than w6.

Knowing that a subject is within domain C merely diagnosis coronary artery disease without providing a clue to the cause. Knowing that a subject is within domain REFAD provides a diagnosis associated with cause, namely a body composition too high in saturated fat. Thus, this invention provides both a disease diagnosis and a means to identify the cause of the disease.

Adipose tissue analysis shows that P4 has plenty of fat, mostly saturated fat. Although he has adequate storage of EFA, he has too much saturated fat. The saturated fat alters the biochemistry of the EFA and produces a biochemical shift that increases the production of 20:3w9. After eating two tablespoons of soybean oil for 8 weeks, and restricting the intake of saturated fat and calories, he returns. He has lost weight and the new analysis shows that his plasma EFA has increased, total cholesterol and triglycerides have decreased, and DEFA has increased in proportion to the EFA eaten. Therefore, he is not suspected of having a metabolic block. Domains representing the variables under discussion (not shown) are used to determine the relative position of P4 vs healthy subjects on said variables. The recommendations are: a) lose weight (eat less and exercise more to burn the excess saturated fat); b) eat meals low in saturated fat and high in polyunsaturated fat (EFA). This diet may prevent further cardiovascular complications, improve overall well being, lower total cholesterol, triglycerides and blood pressure.

P5. Example of Subject with an w3 REFAI

Mr. P5 is a 52 year old white male physician, 5"8", 160 lbs with cholesterol of 190 (about average), triglycerides of 110 (about average), Blood pressure 120/80 (about average), considered to be in good shape, but who is afraid that his biochemical parameters are only within the "normal or average limits", and who is aware that the "average" male dies of heart disease at an early age. He wants to remain very healthy and active into his 90's. He wants to know what he can do. He states that he eats healthy balanced meals.

When compared with men his age, the results of the analysis show that his values are within the domain of the healthy subjects. But when compared with very healthy younger men (domain not shown), he is found to have slightly elevated $FA_c$, a percent of EFA below the range for young healthy men, a mildly elevated 20:3w9, and decreased total w3 (using domains that represent those variables). Adipose tissue analysis shows that he has adequate amounts of fat, but it is mostly saturated fat. The ratio DFA3/PFA3 is proportionately more elevated than DFA6/PFA6=D6/P6 and $R_{3366}$ is mildly elevated. His characteristic pattern is close to the one of subjects with REFAI and with a higher deficiency of w3 than w6.

He is diagnosed as having REFAI when compared with a younger group, but average health according to his age. Moreover, the fact that the D3/P3 ratio is higher than the D6/P6 ratio indicates that the deficiency of w3 fatty acids is much greater than the one of w6 fatty acids. Because he indicates that he would like to be closer to the younger than the older group, he is fed two tablespoons of soybean oil (high in w3) for 8 weeks, and then returns. The new analysis shows that his plasma EFA has increased, total cholesterol and triglycerides have decreased, and DEFA has increased in proportion to the EFA fed. Therefore, he is not suspected of having a metabolic block. The recommendations are: a) lose weight (eat less and exercise more); b) eat meals low in saturated fat and high in polyunsaturated fat; c) eat meals high in w3 fatty acids, such as selected green vegetables, soybean products, walnuts, and fish. This approach may bring his cholesterol levels below 150, and his multidimensional point within the domain of the younger group. His clinical parameters (such as blood pressure) will also move closer to those of a younger group.

P6. Example of Subject with DAF3 REFAI and a Partial Metabolic Block

Mr. P6 is a 68 year old white male, 5"7", 167 lbs. (overweight), with cholesterol of 270 (high), triglycerides of 180 (high), blood pressure 140/90 (mildly elevated), who complains of occassional shortness of breath when exercising, but otherwise considered to be in good shape.

The results of the analysis show that he has elevated FAc (as expected, because of his elevated lipids), a percent of EFA within the Insufficient range, a percent of SatFat above the normal range, a mildly elevated 20:3w9. His characteristic pattern is most similar to the C domain and the domain of subjects with REFAI, and the domain of subjects with metabolic blocks that impede the convertion of EFA to DEFA, more specifically PFA3 to DFA3 (point P6 in FIG. 8C described below).

He is diagnosed as having REFAI. Adipose tissue analysis shows that he has plenty of fat, mostly saturated fat. Although he has adequate storage of EFA, he has too much saturated fat which interferes with the biochemistry of the EFA. After eating two tablespoons of soybean oil for 8 weeks, he returns (point P6' in FIG. 8C). The new analysis shows that his plasma EFA has increased, total cholesterol and triglycerides have decreased, but DEFA has not increased in proportion to the EFA fed, more specifically, he is found deficient in DFA3. Therefore, he is suspected of having a partial metabolic block that limits the convertion of PFA3 to DFA3. The recommendations are: a) lose weight (eat less and exercise more); b) eat meals low in saturated fat and high in polyunsaturated fat; c) eat meals high in fish and fish oils (high in DFA3). This diet will bypass the metabolic block, may prevent further cardiovascular complications, may improve overall well being, lower total cholesterol, triglycerides and blood pressure.

P7. Example of Subject with High Levels of DFA3 and Bleeding

Ms. P7 is a 24 year old white female, PhD student in philosophy, who reads many nutrition magazines and follows the latest diets and fads. She is 5"2", 105 lbs with cholesterol of 125 (low), triglycerides of 50 (low), blood pressure 110/65 (low-average), considered to be in good shape, runs 5 miles every day, but complains of easy bruising and mild anemia. All her previous biochemical studies have been normal and her doctors have not found anything wrong with her. They think her mild anemia is just normal, probably due to her "menstruation". They referred her to a psychiatrist for evaluation and training because she is believed to hurt herself (and cause those bruises). She comes to the inventor for further evaluation. She indicates that about one year ago she read about the benefits of fish oils and fish. She regularly buys many pills and fish oil capsules at health food stores and takes plenty of nutrition pills (but she is not sure what all those pills have).

When compared with women her age (FIG. 7C), the results of the analysis show that her values are within the domain of the healthy subjects, except that she has elevated levels of DFA3. The ratio DFA3/PFA3 is proportionately more elevated than DFA6/PFA6 and R3366 is elevated. The ratio of 20:5w3/20:4w6 (which correlates well with platelet aggregation and bleeding time, subjects with low values of that ratio have high platelet aggregation and low bleeding time) places her within the domain of subjects with hypocoagulation, that is, people who bleed easily. Because her platelet count is normal, she is within the domain of subjects with hypocoagulation not due to low platelets. She does not take aspirin nor other anticoagulation drugs. This restricts her characteristic pattern to the domain of subjects who have bleeding because of a high ratio of 20:5w3/20:4w6.

She is diagnosed as having high levels of DFA3 (because of her diet), leading to decreased platelet aggregation, easy bruising, and high blood loss during her menstruation. The treatment recommended is to eat balanced meals and avoid fish oil supplements. She returns six months later. She is less anemic, no longer has bruises, and her DFA3 has returned to the healthy domain.

Alternative Diagnosis Approach

Easy cases can sometimes be diagnosed using tables (equivalent to multidimensional domains) that compare the values of multiple variables as shown below (a table is like a multidimensional rectangular domain):

TABLE 3

| Type of Subject | Fatty Acid Variables (percent or concentrations) | | | | |
| --- | --- | --- | --- | --- | --- |
| | $20:3w9_p$ | $PFA6_p$ | $FA_c$ | $DFA3_p$ | (D3/P3)/(D6/P6) |
| P3 AEFAI | High | Insuff | Low | Normal | Normal |

TABLE 3-continued

| | Fatty Acid Variables (percent or concentrations) | | | | |
|---|---|---|---|---|---|
| Type of Subject | $20{:}3w9_p$ | $PFA6_p$ | $FA_c$ | $DFA3_p$ | $(D3/P3)/(D6/P6)$ |
| P4 REFA1 | High | Insuff | High | Normal | Normal |
| P5 w3 Insufficiency | High | Insuff | Normal | Low | High |
| P6 DFA3 block | High | Insuff | High | Very low | Low |
| P7 DFA3 excess | Low | High | Normal | Very high | High |

Note: This table is used for illustration purposes; the actual values of the variables depend on the domains used and the measures of distance considered. The diagnosis involves the simultaneous consideration of several variables.

Examples of Diagnosis-Verification Using a Test Mixture

Example of Possible Block.

Mr. B initial diagnosis indicates that he has a block in the conversion of PFA6 to DFA6. The subject eats a test diet high in PFA6 but extremely low in DFA6 for several weeks and the characteristic pattern is determined at various intervals. Changes in the index after taking the mixture serve to verify the diagnosis. If the subject indeed has a block, the new measurements will indicate that plasma levels of PFA6 have increased while those of DFA6 have not; a subject without a block would have converted the PFA6 to DFA6.

Example of Malabsorption

A Patient has reduced EFA levels in blood. Is it because he does not eat enough EFA or because he cannot absorb them? Feeding EFA solves the problem: If EFA levels increase after eating EFA, the deficiency is due to lack of eating; otherwise it is due to poor absorption.

Comparison with Miyagi Patent and Current Diagnosis

Figure 7:
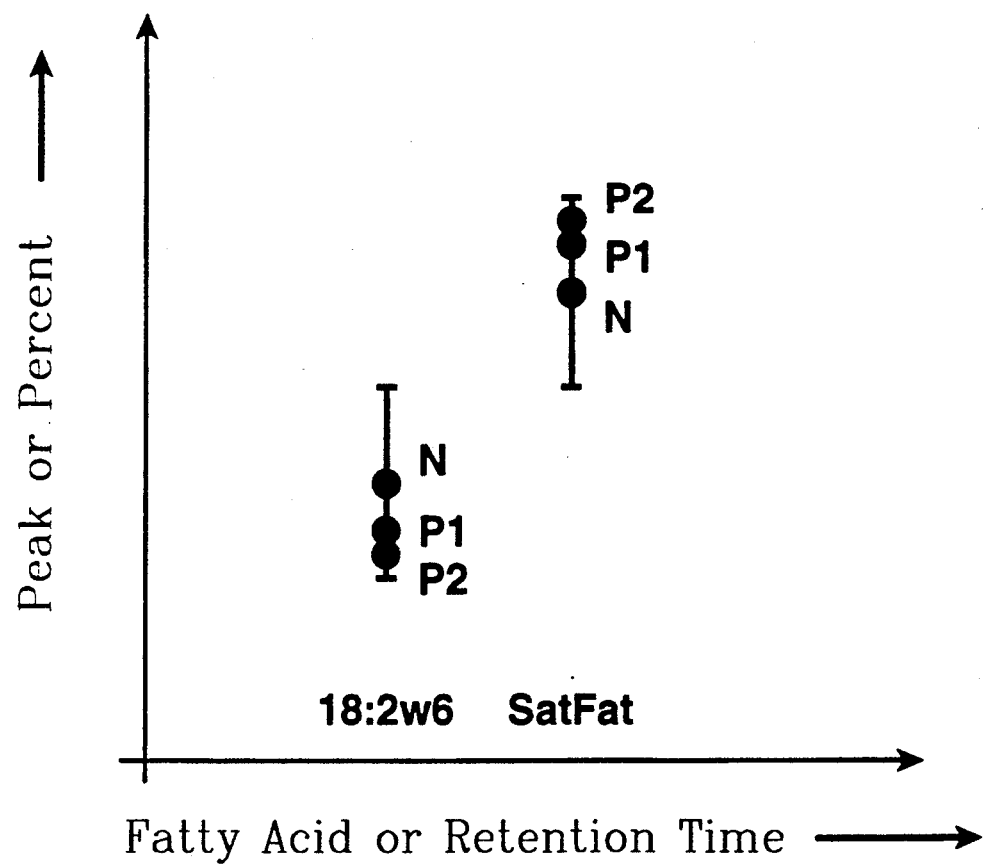
FIG. 7A is a comparison of the diagnostic value of the current invention versus alternative unidimensional approaches. The figure shows that patients P1 and P2 are incorrectly diagnosed using a diagram such as the one of the Miyagi patent or the one used by current medical diagnostic methods.
FIG. 7B is a diagram which shows that concurrent use of additional tissue provides a different diagnosis than the one arrived from the analysis of one tissue.
Figure 7:
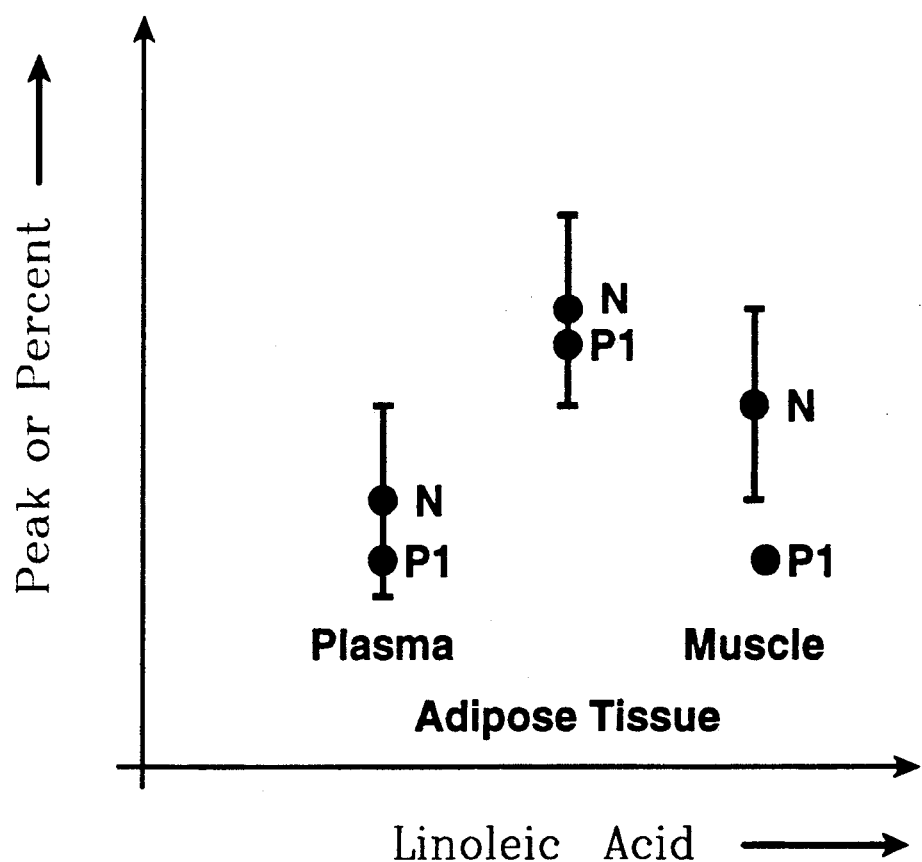

FIG. 7A compares the present invention with the Miyagi patent using two fatty acids, linoleic acid (PFA6) and any other fatty acid such as total saturated fat (SatFat), for which peaks have been measured. The Miyagi patent refers to peak areas which, for ilustration purposes, will be considered to be percents (it really does not matter whether they are percents or concentrations).

The Miyagi patent (FIG. 7A) would diagnose P1 as healthier than P2 because P1 is closer to N than P2 for each fatty acid. A similar result is reached with a two dimensional representation of reference ranges (see FIG. 6B). In contrast, the present invention (FIG. 5B) would classify P2 as healthier than P1 because P2 is inside the healthy domain while P1 is outside.

This illustrates the fact that two-dimensional domains as proposed in this embodiment provide a diagnosis different than the one obtained by merely extrapolating conventional diagnosis based on ranges to two dimensions.

The present invention describes different types of multidimensional spaces used to correctly diagnose disease. The Miyagi diagram, although two dimensional in appearance, has only one dimensional variable, namely the peak of a given substance. FIG. 7B explains that the Miyagi patent refers to body fluids and appears to exclude other tissues. The present invention, by comparing plasma with adipose tissue levels, diagnoses diseases that cannot be diagnosed with the Miyagi patent. In FIG. 7B a subject has normal plasma levels, low adipose tissue levels and abnormal muscle cell production of 20:3w9, consistent with insufficient levels of EFA at the cell level.

Embodiment of the Apparatus

An embodiment of the disease diagnostic apparatus adapted for the practice of the method of disease diagnosis shown in FIGS. 1 through 4 will be described with reference to the flow chart shown in FIG. 9.

The apparatus consists of the following parts (FIG. 9A): 1) A Data Input Unit (DIU), which in this embodiment is a keyboard and is labeled as "data Entry", but could be a cable connecting this apparatus to another instrument; 2) A Memory Unit (MU), which in this embodiment consists of a hard disk ("Hard Disk Memory"), but can consist of any type of long and short term storage devices; 3) A Central Processing Unit (CPU), which processes the information and in this embodiment consists of the processing unit of a computer (and incorporates the electronics to transfer and temporarily store information from and to any of the other parts); 4) a display unit (DU), which in this embodiment is a video display, but could be one or more displays such as printers and plotters; 5) means for connecting said parts and transferring information from one part to another, which in this embodiment consists of the circuitry to connect the keyboard to the hard disk, the video display and the CPU (symbolized by the arrows indicating two directional communication); 6) A computer program to perform the steps described in the embodiment of FIG. 9B.

The user prepares the data that describes the healthy and disease domains, and other domains, including hypothesized metabolic disorders. These data on the domains for healthy, disease and other types of subjects are stored on the Hard Disk. The user enters data regarding the test subject characteristic pattern on the keyboard. The user enters specific concentrations and/or percents of substances, which in this embodiment consist of fatty acids and lipids as previously described. The apparatus ask the user what domains he wishes to consider, and requests information about the characteristics of additional domains describing metabolic disorders, such as the domains of subjects with relative and absolute deficiencies of Essential Fatty Acids. The apparatus displays a list of possible variables and the user selects the variables to consider. Alternatively, the user may enter any formula to define a new variable. Examples of variables are provided in FIGS. 2 and 3.

Figure 4:
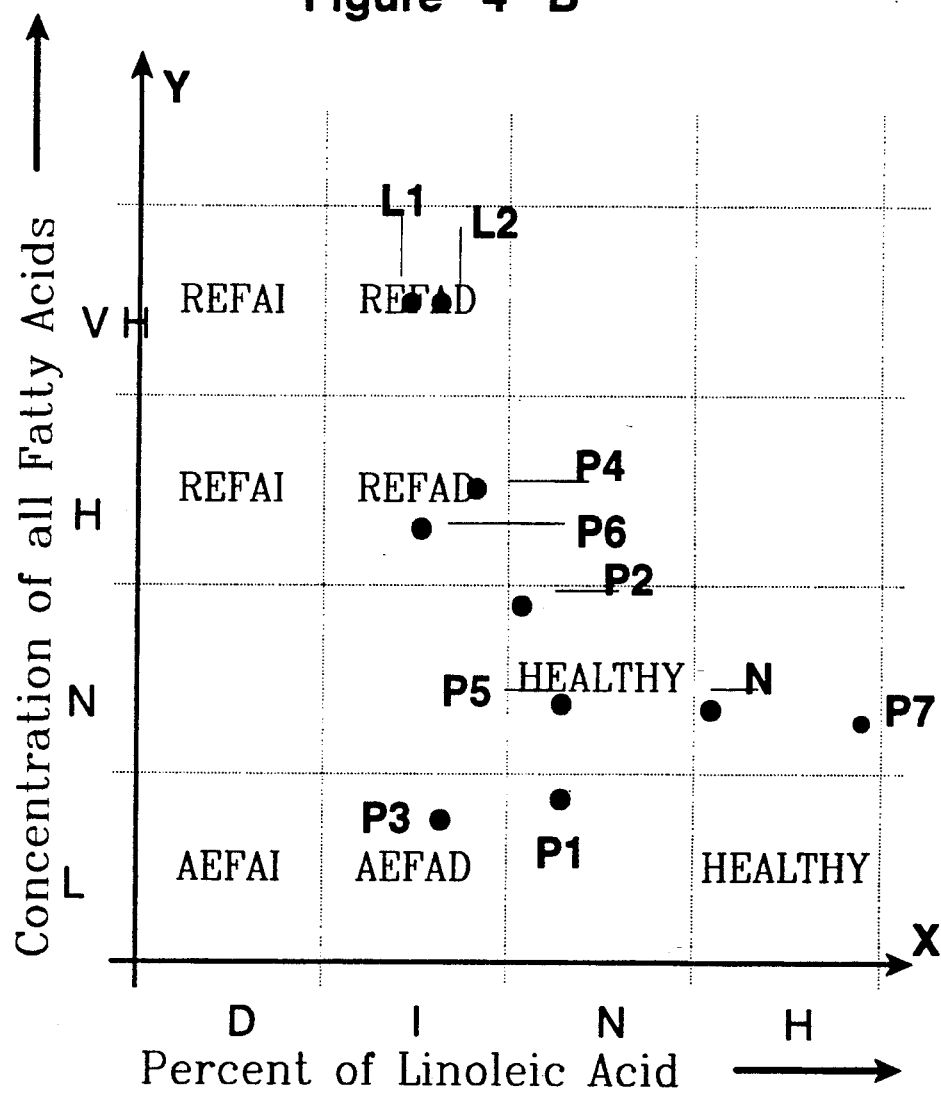
FIG. 4A illustrates the theoretical metabolic domains representing Relative and Absolute Essential Fatty Acid Deficiency and Insufficiency. The X-axis has four areas corresponding to Deficient ("D"), Insufficient ("I"), Normal ("N") and High ("H") levels of linoleic acid. The Y-axis has four areas corresponding to Low ("L"), Normal ("N"), High ("H") and Very High ("VH") levels of total plasma fatty acid concentration (similar to total lipid concentration). Light dotted lines divide rectangular domains.
FIG. 4B adds several patients (letters "P") to FIG. 4A.

The apparatus also offers a choice of alternative measures of distance or similarity among domains. Alternatively, the user may enter his own measures of distance or similarity. For this particular embodiment, the measures of distance are the ones described in the previous embodiment (FIG. 1), namely the distances between the geometric centers of mass of each domain, and the distance between the multidimensional point of the test subject and the center of mass of each domain. For this embodiment only two dimensional domains such as those illustrated in FIG. 4 are considered.

The apparatus compares the multidimensional characteristic pattern of said test subject with the healthy domain stored in the hard disk. If the test subject pattern (a point in two dimensions) is inside the healthy domain, the subject is considered healthy and the apparatus displays the results of the analysis. If it is outside, the apparatus calculates the distance of said test subject to each disease domain and then calculates the probabilities of each disease and displays the information on the video display. The probabilities of each disease are calculated as the inverse of the distance as previously indicated. The apparatus then displays, for each disease domain, the probability of the disease and other results as indicated in FIG. 9B.

The user is then offered an opportunity to change his choice of axes and the apparatus displays data on any two axes on the screen, or may display multidimensional diagrams if the user specifies more than two axes. Alternatively, the user may specify projections of a multidimensional space on any two axes. The user, optionally, may change the scales and scale units on any of the axes to improve the display, or may rotate the multidimensional diagrams. Information displayed on the video display may be transfered to a plotter or printer.

The user may also choose to redefine the variables, or redefine the axes used to calculate the distances between domains and the test subject. The apparatus then recalculates and redisplays the revised disease probabilities and additional data. The user may continue to either view the data using alternative variables, or recalculate the disease probabilities to identify alternative diagnostic options or to better determine what metabolic abnormalities are most similar to the characteristic pattern of said test subject.

The user may then identify possible objectives of the test diet and the apparatus displays the components of such test diet.

Other Embodiments

While the above description contains many specificities, these should not be construed as limitations on the scope of the invention, but rather as an exemplification of one preferred embodiment thereof. Many other variations are possible. For example, the user can specify any variables or transformations among variables; he can determine the type and scope of the domains to be used; he can choose to use one multidimensional domain or several domains of lesser dimensions; he can use a variety of approaches to measure similarity between a test subject and disease domains; he can display the results in a variety of formats, from two dimensional graphs to tables to flow charts. The examples below illustrate additional variations of this invention.

I. Additional Examples of Domains

Other multidimensional domains are obtained by plotting on the axes several of the other indices named before (see FIG. 2 and 3) or by combining in one single multidimensional space all the domains of FIG. 5A, 8A, 8B, 8C, and 8D. Alternatively, several multidimensional spaces can be considered for each group of subjects, each space having at least one different axis (see FIG. 8 for examples of several two-dimensional sets of domains).

Figure 8:
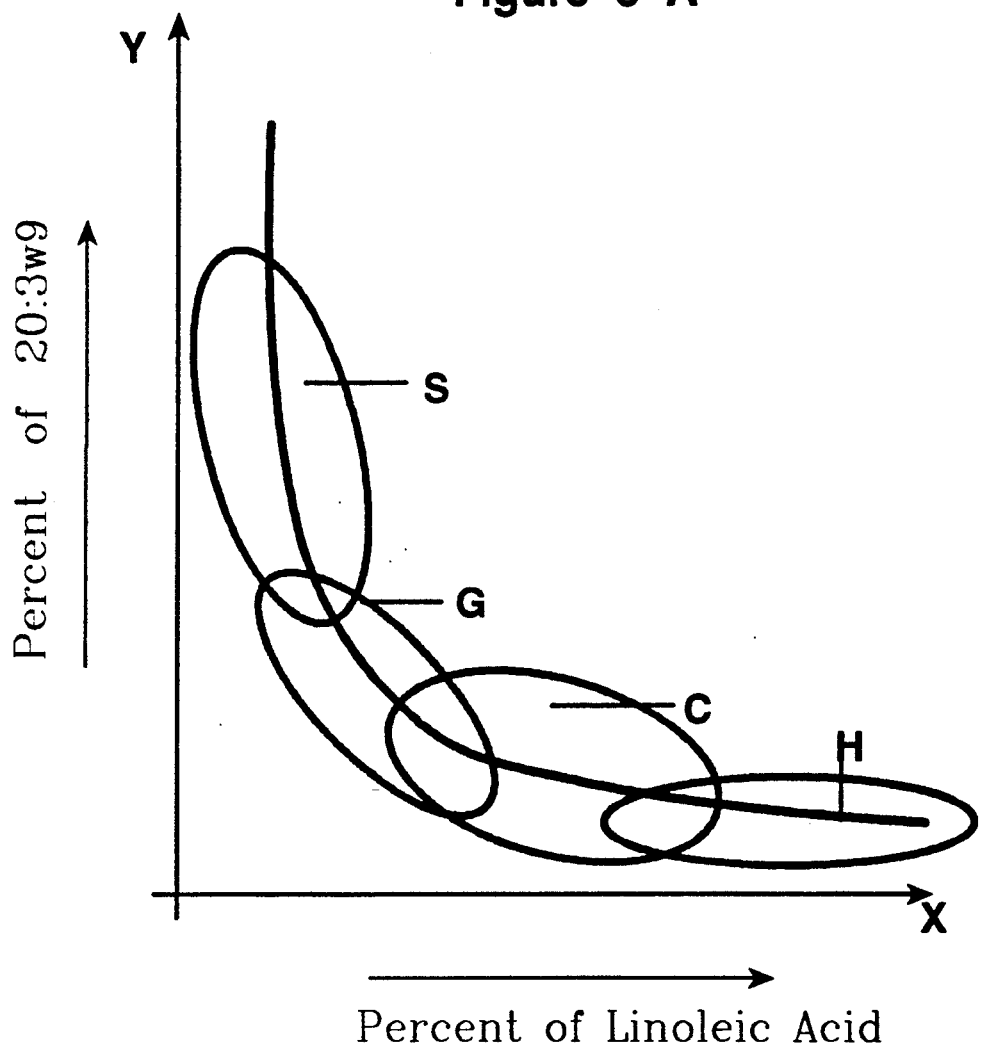
FIG. 8A is a diagram which displays percents of 20:3w9 versus percent of linoleic acid. It is often used in conjunction with other diagrams and distinguishes cell level deficiencies (when cells do not get enough EFA, they increase production of 20:3w9).
FIG. 8B illustrates dietary variations in monounsaturated fatty acids. The diagram shows the expected range (approximately a straight line) of variation of monounsaturated fatty acids over a wide range of total w3+w6. Subjects outside this range (marked by several ellipses indicating domains for several groups) have biochemical abnormalities (see text). M1 and M2 are two patients, M1 has too little monounsaturated fat (probably production defect) and M2 has too much (probably eats too much).
FIG. 8C illustrates dietary variations in metabolic activity. The diagram shows a hypothetical inverse relationship between DFA3/PFA3 and PFA3. The hypothesis is that lower dietary intake of PFA3 lead to lower body levels of PFA3 and increased production of DFA3 to maintain DFA3 body levels. Subjects outside the closed domain have non-dietary alterations. Patient P6 fails to increase production of DFA3 and is therefore suspected of having a metabolic block. P7 represents a patient that eats too much fish oils high in DFA3.
FIG. 8D illustrates dietary variations in lipids. The diagram displays a hypothetical inverse relationship between Cholesterol/Triglycerides versus Triglycerides for subjects with normal genes but varying dietary intake. Subjects outside the domain of dietary variation, shown as a curved ellipsoid, are presumed to have a genetic defect or some organ disease. Patients L1 and L2 have abnormal lipid metabolism leading to abnormal relations between the variables represented in FIG. 8D. The cause is probably a genetic abnormality or an organ disease such as thyroid disease.
Figure 8:
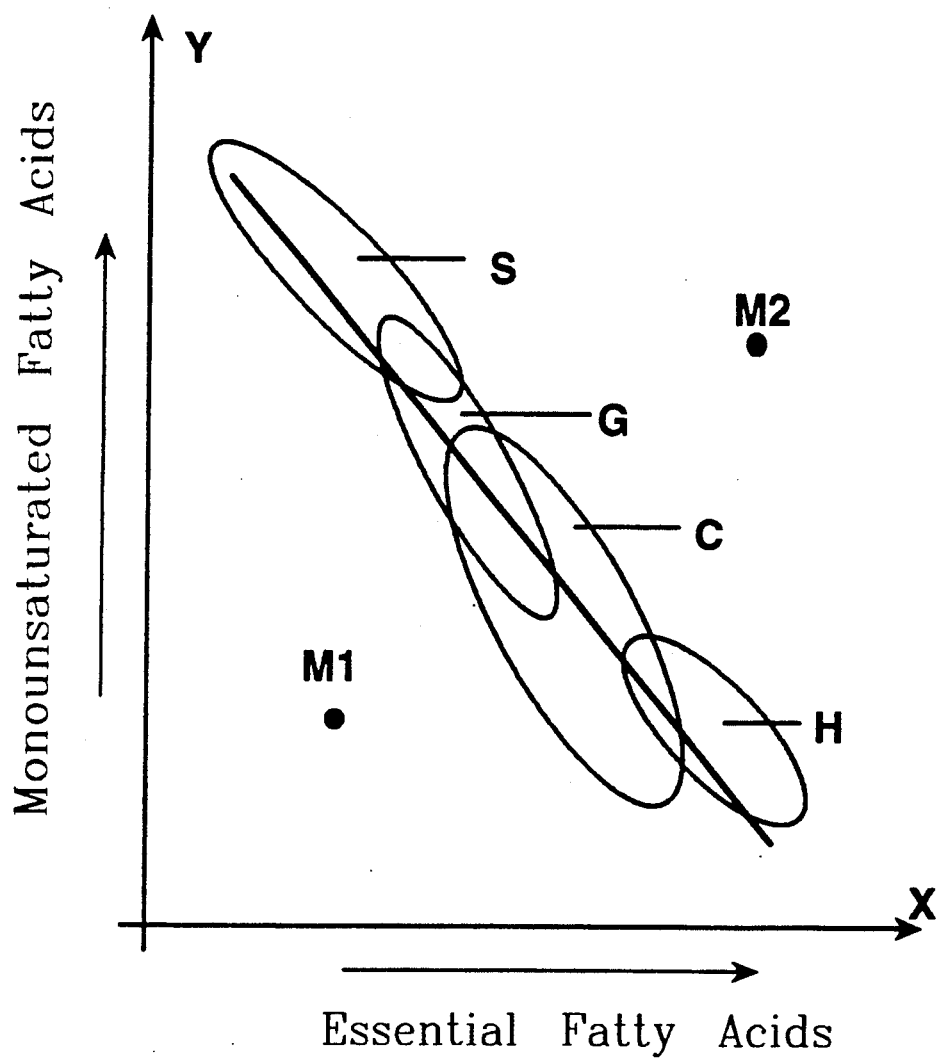
Figure 8:
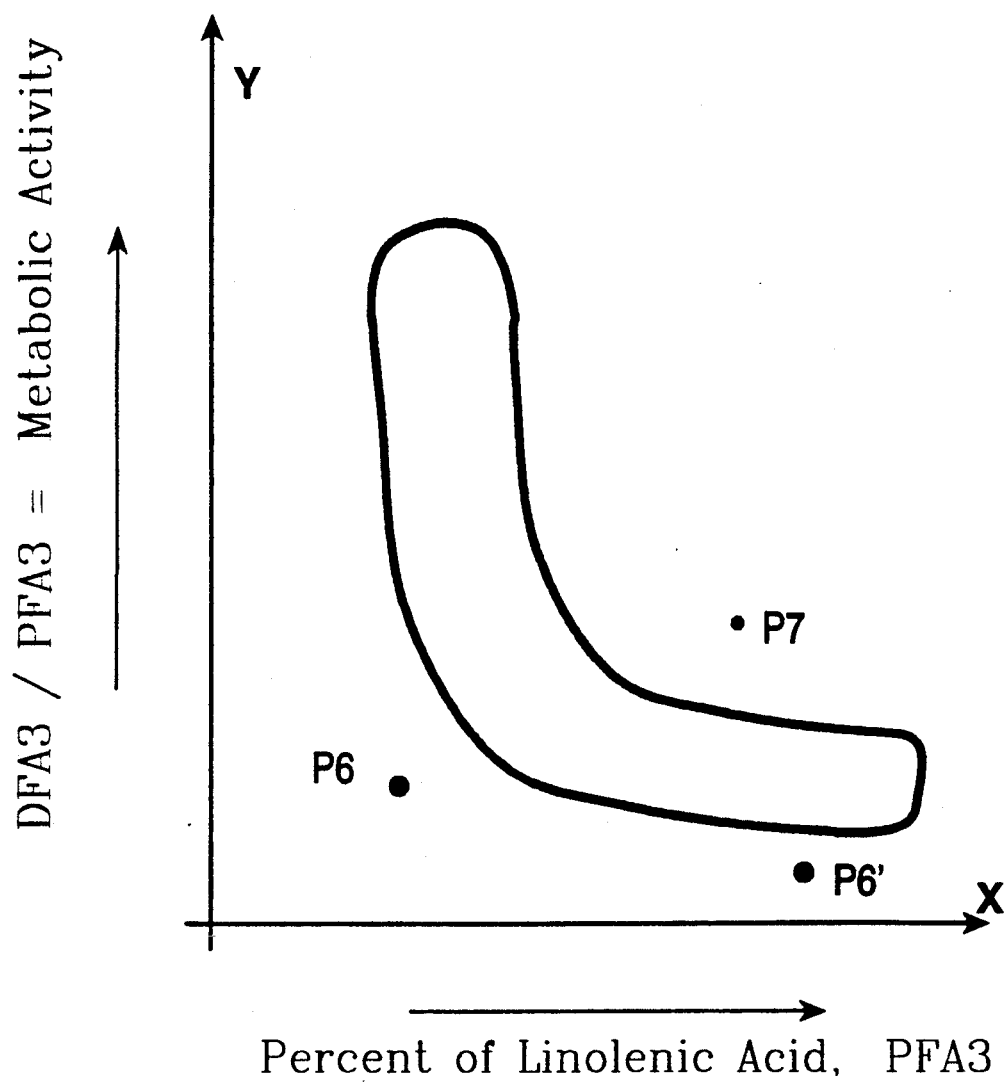

(1) FIG. 8 contains additional examples of two dimensional spaces used for diagnosis.

FIG. 8A plots the variable 20:3w9, a fatty acid that increases when the body is deficient in essential fatty acids, vs percent of linoleic acid. The location of several domains is marked. FIG. 8B represents hypothetical biochemical relationships indicating that the amount of monounsaturated fatty acids is inversily proportional to the amount of EFA in plasma. There is a region that represents the domain of expected variations in EFA and MONO over a wide range of diets. Subject M1 is outside said domain, suggesting a defect in the formation of monounsaturated fatty acids; subject M2, also outside said domain, may eat a diet too high in monounsaturates (FIG. 8B). FIGS. 8A and 8B, alone, do not distinguish well between the groups C and G. Used in conjunction with other diagrams, they improve diagnosis as described in the examples above.

FIG. 8C plots the ratio DFA3/PFA3 vs PFA3. Over a wide range of dietary intake, individuals with less PFA3 have increased pathway activity leading to a higher DFA3/PFA3. Patient P6 (discussed above) has a metabolic block that interferes with the formation of DFA3 (because the DFA3/PFA3 ratio is below the ratio expected for the level of PFA3). Patient P7 (discussed above) has too much DFA3.

The inventor proposes that environmental factors, such as geographic temperature and humidity, and genetics, affect the curves. For example, the curve for blacks in Africa may be below the curve for inhabitants of cold areas, indicating that the conversion to derivatives is more active in cold areas or in cold weather, or is genetically determined.

FIG. 8D indicates that when subjects increase their plasma cholesterol because of dietary factors, triglycerides increase even faster. In this example the hypothesized relation between Total Cholesterol/Triglycerides and Triglycerides is represented by the elongated ellipsoid shown in FIG. 8D. This domain is entered by the user to indicates a range of values which reflects dietary variations. Subjects outside that domain have non-dietary abnormalities, and the location of the multidimensional characteristic pattern indicates the type of abnormality. FIG. 8D also shows, within the bigger domain of dietary variations, the locations of the groups C and H (same groups as in FIG. 4B and 5B). A patient within the domain C has a disease probably due to bad eating; patients L1 and L2 have a disease caused by factors besides bad eating (such as uncommon genes).

(2) A three-dimensional space created with the variables percent of linoleic acid, concentration of fatty acids and percent of 20:3w9 further discriminates among diseases. Consider a subject that has normal to low levels of total plasma fatty acids and normal percent of linoleic acid. Two types of subjects could meet this criteria: a thin person with mild malabsorption following a good diet, and a thin person following a normal diet. Adding 20:3w9 distinguishes these two subjects; the healthy person has almost no 20:3w9 while the malabsorber has high levels of 20:3w9 (note: usually thin people have low plasma lipid levels and therefore low total concentration of fatty acids).

(3) A four dimensional space adding the variable DFA3+DFA6 to the example indicated above. This is useful to diagnose blocks like in FIG. 8C.

(4) Using data for Blacks, Whites, Males and Females this invention prepares a four dimensional space, similar to FIG. 4A, with axes Race, Sex, percent of linoleic acid and concentration of fatty acids.

(5) The physician may enter other data, for diagnostic purposes, on additional axes. A physician may decide to consider the size of the heart as determined by ECG or radiologic examination, and use that size as an additional variable. When data are available on these new variables for healthy and abnormal subjects, they are considered like any other variable (axes) in the multidimensional analysis.

(6) Multidimensional domains obtained by plotting any of the indices or variables previously indicated, and/or the concentration of other substances such as a vitamin, mineral, lipid, protein, aminoacid, carbohydrate, or indices derived from these substances, or the results of quantities of substances measured in different types of tissue.

(7) Multivariate linear regression equations are developed for each concentration variable where the concentration variable is the dependent variable, and the total fatty acid concentration in plasma is the independent variable. Adjusted concentration variables are computed as the residuals in each equation, namely the value of each concentration variable less the predicted value using the total fatty acid concentration in a regression equation.

Example

Let $PFA6_c$ be the concentration of PFA6, and $FA_c$ the concentration of all fatty acids. The regression equation for the group of healthy subjects (i.e., using only healthy subjects) is:

$$PFA6_c = A6_c + B6_c * FA_c$$

(Notice different coefficients for each fatty acid). The term $A6_c$ represents the adjusted concentration of $PFA6_c$, adjusted by the effect of $FA_c$. The reason for doing this adjustments is that the sum of all fatty acid concentrations is equal to $FA_c$. Therefore, in general, each individual $F_{ci}$ is positively correlated with $FA_c$. The adjustment removes this bias. The inventor found no published reference to similar adjustments in concentrations.

A multidimensional space is constructed using the above described variables (in lieu of the regular concentrations). Using the results of measurements of fatty acid percents and concentrations as indicated above, domains are created for each of the subjects in the groups healthy, C, G, S and L. All these data are stored in computer readable media and used for diagnosis as described before. This embodiment of an adjustment to concentrations does not exclude other adjustments.

(8) Multidimensional spaces formed with any of the following variables: the total fatty acids of each family w3, w6, w9, w7, total saturated fat, trans, isomers, and branch fatty acids; the total concentration of individual lipids (such as cholesterol ester); similar values for a tissue fraction other than plasma (such as a lipoprotein particle (i.e., LDL, HDL) or red cell, lymphocytes, or macrophages); the result of other medical test (i.e., blood pressure); or other demographic, sociologic, or clinical data.

(9) Additional variables such as the mean value of each group (the $G_k$ divided by the total number of components included), the geometric mean, and those computed with other formulas. The more general rule is that a variable V is created as a function of the measured quantities of a given set of nutrients: V=f(Nutrient 1, . . . , Nutrient n).

II. Alternative Measures of Distance

Alternatively, discriminant, baysian, and canonical analysis is used to calculate indices of similarity and difference between each domain and said test subject. These indices of similarity are equivalent to the distances Dk. Moreover, these indices may be calculated without first testing whether the subject is inside or outside the healthy domain. D. R. Bock, in a book titled "Multivariate Statistical Methods in Behavioral Research", McGraw Hill Co, N.Y., 1975, explains how to solve the problem of assigning probabilities that a test subject is most similar to subjects of a given domain. The problem is phrased as follows: a) a subject is known to belong to one of n populations (domains); b) the relative sizes of the populations are known; c) there is information about each subject in the form of a p-component score vector (the indices); d) the density function of each population is known (based on the index values of each subject of each domain).

Any of a variety of commonly used statistical techniques for multidimensional analysis can be used to compute distances between said test subject's characteristic point and the healthy and disease domains. Under these circumstances, it is not necessary to test first whether the subject is inside the healthy domain. The apparatus described calculates the probability of being healthy or having any of a set of diseases.

Example

Instead of the geometric center of mass, weighted values are assigned to each individual point to calculate a center of mass for each domain. The weights represent the degree of certainty or error associated with each individual point, or the perceived importance, by the user, of each measurement. The user may input a set of weights for different indices or use equal weights as the default value. The calculations of previous steps are repeated using these weights. Using errors as weights, values that have a smaller error have a higher weight. An example of a weight is the inverse of the error, with a user established upper limit for the error.

III. Other Measurement Techniques

The present invention is equally applicable to concentrations of substances measured by a variety of techniques, including chromatography such as HPLC, GLC, TLC, gel permeation and immunology techniques.

IV. Preservation of Tissues

In the practice of this invention the tissue sample, including blood and cell samples, taken from a subject, may be used fresh or may be stored in frozen condition until it is convenient to analyze the sample.

V. New Diseases

The multidimensional point of one patient may fall outside the domain of any of the currently known diseases. Sometimes the displayed information indicates that none of the currently stored domains has high similarity with said patient. In that case, based on knowledge of biochemical pathways, users may enter data representing domains that reflect the effect of theoretical modifications in the biochemical pathways. These domains compete with other domains for diagnosis, and said patient may be closer to a domain representing a new disease, than to a domain associated with previously analyzed disease subjects. Alternatively, new diseases may be discovered in the future, leading to additional domains. The invention remains the same: the results of one subject are compared with domains representing disease states.

Example of Lipid Transfer Defect

Mr. L1 is a 34 year old patient with symptoms of premature coronary artery disease and high cholesterol and hyperlipidemia of unknown origen which has not improved with conventional medication (see FIG. 8D). Mr. L1 absorbs the fatty acids which are stored in triglycerides but, due to a genetic enzyme defect, he does not form cholesterol esters from phospholipids. In this case, the amount of EFA, after meals high in EFA, will be high in triglycerides and phospholipids, but will remain low in cholesterol esters. In this manner, the analysis of lipids (triglycerides and cholesterol esters in this case), and fatty acids in lipids, helps to establish the diagnosis.

The percents of selected fatty acids in two lipids, Cholesterol esters and Phospholipids, when compared with ranges of a healthy population, are shown in Table 4:

TABLE 4

| Lipids | Pattern of Percent of fatty acids in patient L 1 | | | | |
| --- | --- | --- | --- | --- | --- |
|  | PFA3 | DFA3 | PFA6 | DFA6 | 20:3w9 |
| Cholesterol esters | Low | Low | Low | Low | Low |
| Phospholipids | High | Low | High | Low | High |

Published studies have shown that fatty acids are transfered from phospholipids to cholesterol esters, and that cholesterol esters carry them inside cells. A block in the transfer of fatty acids from phospholipids to cholesterol esters may prevent cells from obtaining adequate amounts of EFA. To adapts cells will synthetize more 20:3w9 and will also signal the body to send more EFA to the cell. When the person eats EFA, plasma EFA would rise because the EFA is absorbed. Thus, under the assumption of a block in the transfer of fatty acids, a new domain is created associated with the disease: "Lipid transfer defect". Subjects in this domain have high percent of EFA in phospholipids, low percent in cholesterol esters, high 20:3w9 in plasma and high plasma EFA. Alternative hypotheses may be generated to explain observed data. A test diet may then be used to confirm a diagnosis.

This patient L1 has a multidimensional point closest to the "Lipid transfer defect" domain. Using this invention the diagnosis is made that the transfer of the EFA (PFA3 and PFA6) from Phospholipids to Cholesterol Esters is defective. The defect is probably genetic, but could be overcomed with large amounts of EFA and DEFA. A test mixture is prepared and used to determine the best treatment as indicated in previous examples.

VI. More Intermediate Pathways

The reaction from PFA to DFA actually proceeds through many steps. The examples illustrated before combined all fatty acids after the precursor fatty acid (PFA), into one group, the derivative fatty acids (DFA). This is not necessary. The ratios of the concentration (or percents) of one fatty acid to the one preceeding it are used to identify blocks in specific steps. A block may be identified in any one of the multiple steps that convert one fatty acid into another.

VII. Classification of Hyperlipidemias

Medical textbooks classify hyperlipidemias into groups according to the results of lipids measurements (excluding fatty acids). This invention proposes an alternative classification. The results of lipid and fatty acid measures are used to produce a different classification (the domains for each disease). This classification allows a physician to identify the particular biochemical defect which produces a domain closest to the subject under consideration. He may then treat it with a test mixture to see if the treatment moves the subject's multidimensional point closer to the healthy domain, and in this way further identify the diagnosis and the optimal nutritional treatment. Another example of a possible genetic disease is patient L2 in FIG. 8D, who has triglycerides so high that it is outside the domain of dietary variation represented by the enclosed area in FIG. 8D.

VIII. Metabolic Blocks (Simple Case)

The above procedures are modified as follows. The variables used to create the multidimensional domain are PFA3, PFA6, DFA3 and DFA6. The diagram will show that a test subject such as P6 with a metabolic block (see FIG. 8C) has little DFA6. First the subject is treated with a mixture of PFA3 plus PFA6 designed to bring his PFA3 and PFA6 values within the healthy domain. This mixture should also bring the DFA3 and DFA6 values and other fatty acid parameters within the healthy domain IF there is no metabolic block and the deficiency of DFA6 is due to a deficiency of PFA6 (similarly for w3). When the subject with a metabolic block is retested and a new diagram is created, it will show a large increase in the precursors and very little increase in the derivatives (DFA3 and DFA6). Given that the subject has a disease that indicates the presence of a block in the formation of DFA from PFA, the DFA after the block is provided.

For example, after eating PFA3 and PFA6 for several weeks, the subject is found to have plasma levels of DFA6 within the healthy domain, but plasma levels of DFA3 outside the health domain and low. To correct, a new diet is prepared with supplements of DFA3.

IX. Other Diets

The preparation of the test and treatment diets may be done according to a variety of formulas. For example, a diet may include more EFA than the amount calculated by the above formula in order to achieve a faster change in body composition. It may consist of a mixture of PFA and DFA, or several of the intermediate metabolites. In the future commercial production of derivatives of the EFA may produce a wide variety of fatty acid metabolites. Vitamins and minerals may be added to prevent fatty acid oxidation and correct other nutritional inbalances.

X. Types of Axes

Examples of variables for each axis were shown in FIGS. 2 and 3. The invention also considers the exclusion of certain variables, either because they may produce misleading results or because another variable provides improved diagnosis. In particular, one of the two-dimensional embodiments excludes from the X-axis the following variables percent: linoleic acid (18:2w6); EFA+DEFA/Sat.Fat+MONO (referred to as EFA/-NOEFA in reference AJ FIG. 2); Total w3+Total w6.

The same embodiment excludes from the Y-axis the following variables percent: 20:3w9/20:4w6; 16:1w7; MONO; Total w9+Total w7.

Figure 5:
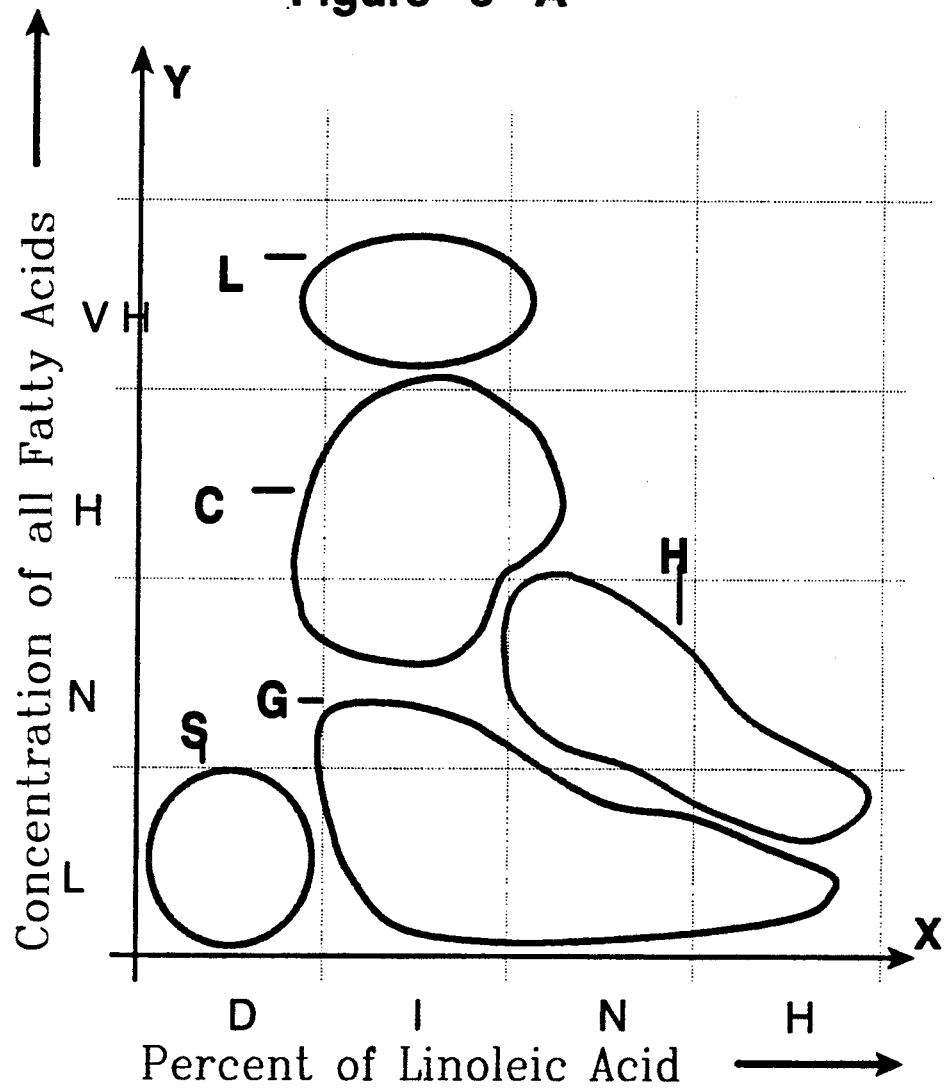
FIG. 5A illustrates domains in a two dimensional space representing the relationship between percent of linoleic acid and concentration of all fatty acids. The domains are the smallest area (shape irregular) that includes all the subjects in one group. The letters identify each group as the Severe Deficient ("S"), Gastrointestinal Disease ("G"), Coronary Artery Disease ("C"), High Lipids ("L") and Healthy ("H")
FIG. 5B adds several patients (letters "P") to FIG. 5A.
Figure 5:
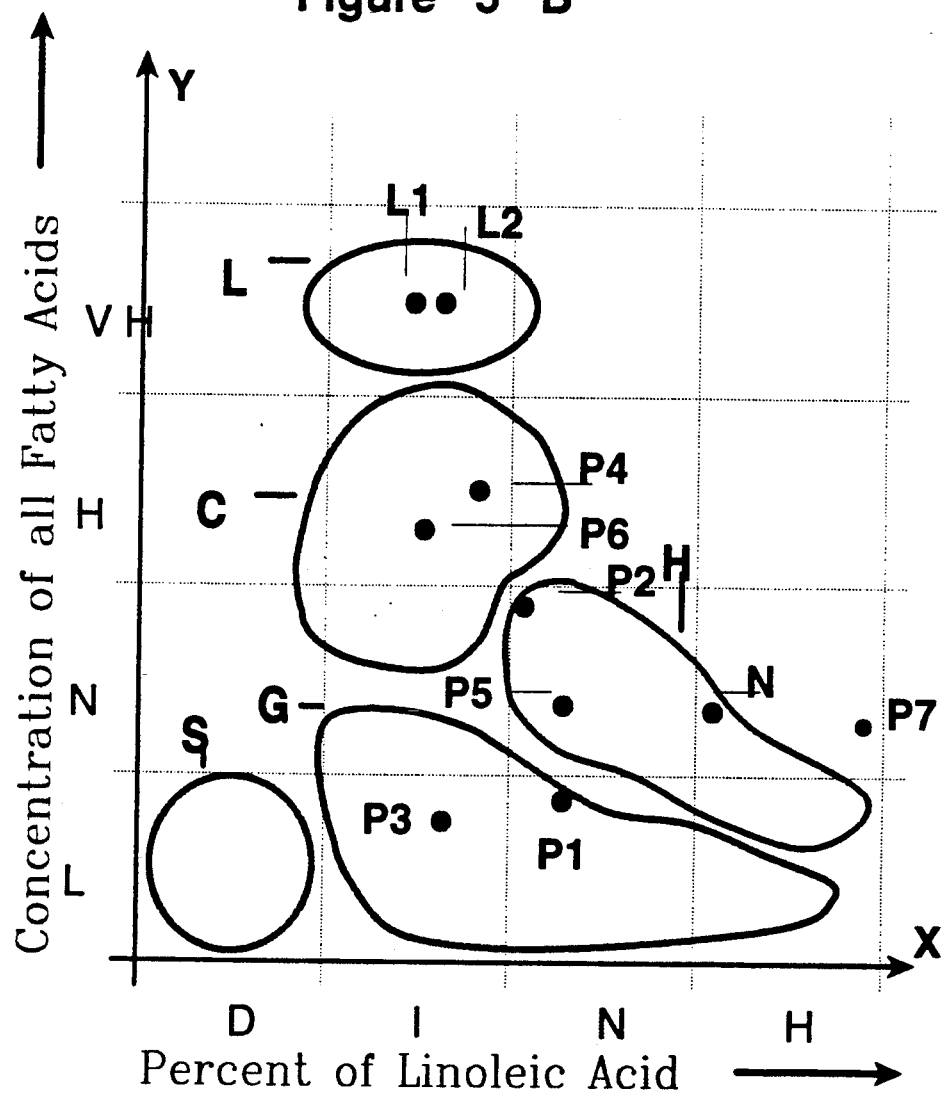
Figure 6:
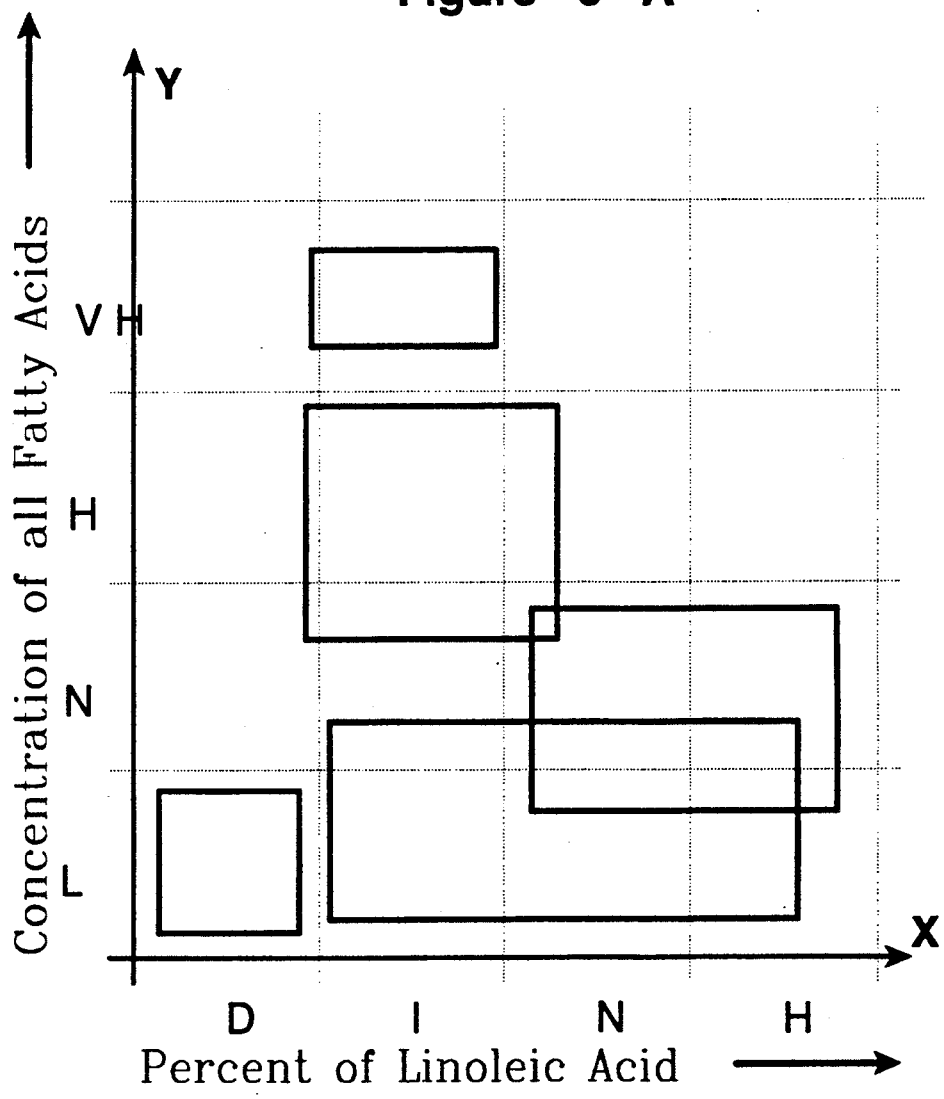
FIG. 6A illustrates ranges in a two dimensional space representing the relationship between percent of linoleic acid and concentration of all fatty acids. These ranges represent the traditional approach to diagnosis on the basis of normal ranges in individual variables. Using the two dimensional ranges on each axis, a rectangle is formed for the Healthy Domain. Similar rectangles are constructed for the other domains. The rectangles have maximum dimensions smaller than the domains because they are formed with the mean ± the standard deviation, and therefore include about 95% of all subjects.
FIG. 6B adds several patients (letters "P") to FIG. 6A.
FIG. 6C compares the effect of ranges with domains (superimposed FIG. 5B and 6B).
Figure 6:
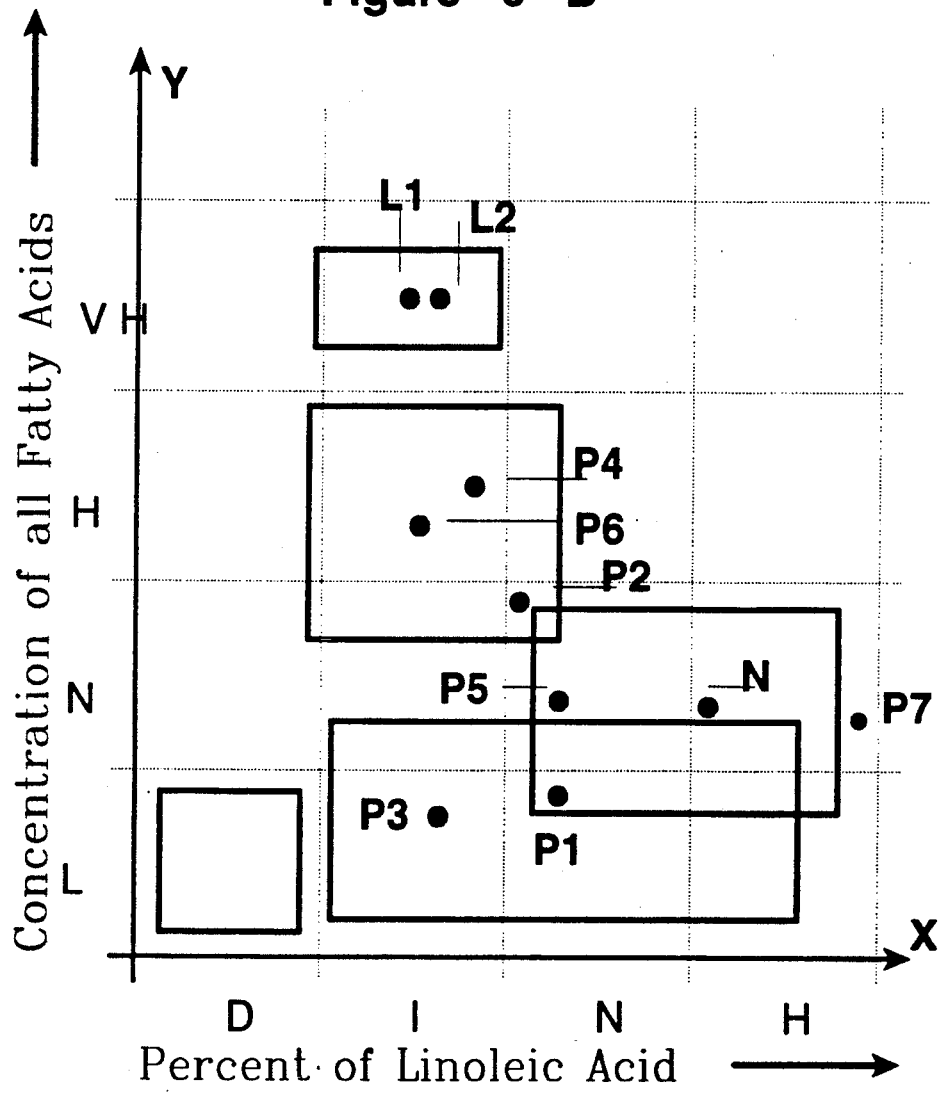
Figure 6:
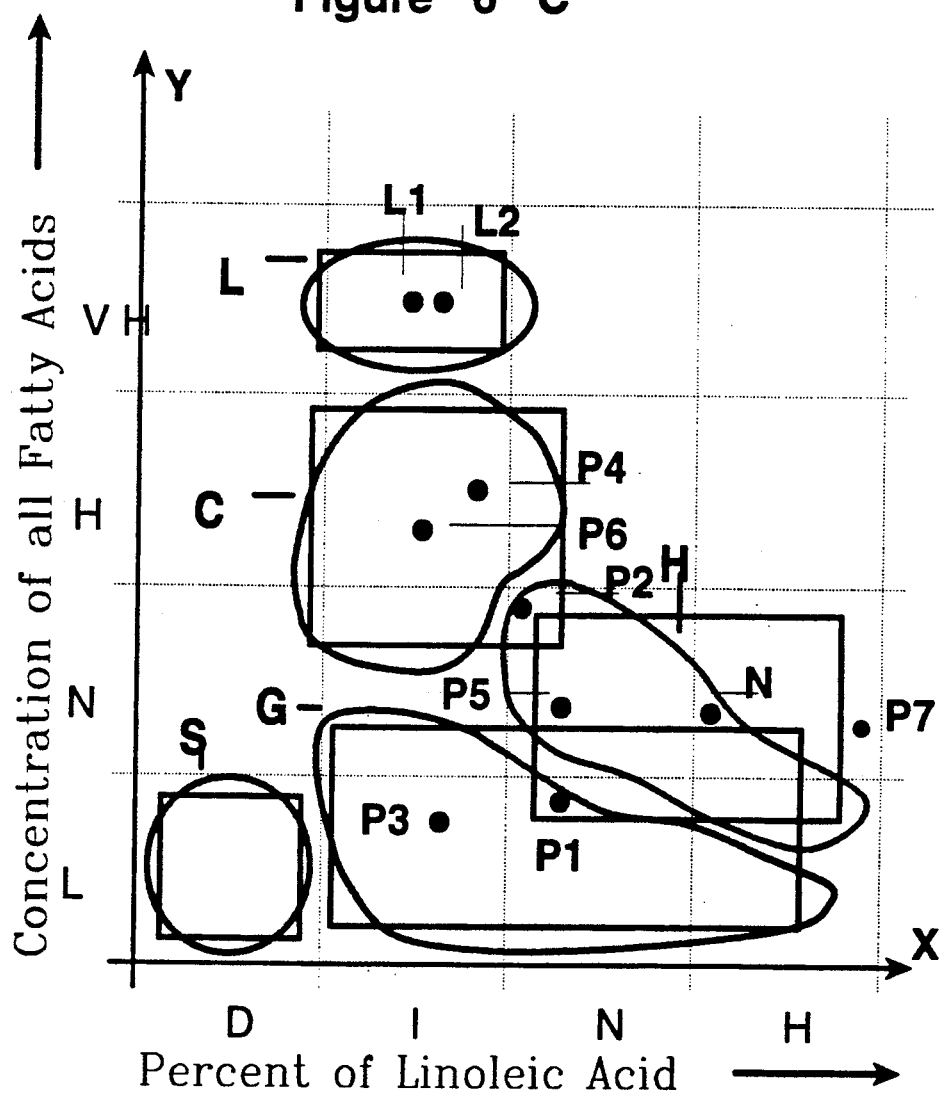

Notice that TIME (i.e., weeks, days, hours) is not considered a variable for the purposes of this invention and therefore two-dimensional graphs with time in one axis are excluded (such as those in reference AJ, FIGS. 3-5).

XI. Other Substances

Fatty acids may be measured in whole plasma, serum, red cells, white cells, adipose tissue, lipoproteins such as High Density Lipoprotein ("HDL"), lipids. The invention does not require a specific type of sample. The term lipid is used as defined in biochemistry textbooks, to include phospholipids, cholesterol esters, triglycerides, and glycolipids. Lipids may contain fatty acids. For example, a triglyceride has three fatty acids, a phospholipid has two and a cholesterol ester has one fatty acid. Derivatives of fatty acids include their esters and biochemical metabolites.

In other embodiments, the invention uses the concentrations or the percents of the following substances: 1) aminoacids, using the total identified aminoacids; 2) vitamins and minerals, using the total vitamins or minerals; 3) lipids, such as cholesterol ester, phospholipid, triglycerides, as a percent of the total lipids; 4) fatty acids within each lipid class. From the percents and concentrations of each substance indices are computed according to the steps described above for the fatty acids. Derivatives of fatty acids and lipids are used because it is often practical to measure a derivative rather than the actual fatty acid or lipid.

CONCLUSION AND SCOPE OF INVENTION

This invention is a new process to diagnose abnormalities of lipid and fatty acid metabolism. The reader can see that this invention produces different and more accurate diagnosis than currently used methods. A key difference with prior art is the ability to use alternative patterns to calculate the probabilities of different diseases, including suspected or hypothesized biochemical abnormalities. This invention can identify the cause of the disease. It can also be used to determine the optimal nutritional treatment.

This invention differs from traditional diagnostic procedures whereby the diagnosis is based on the values of one or more substances and those values, considered as normal or abnormal, are defined independently from each other for each one of such substances (previously referred to as one-dimensional ranges). For example, it is traditional in medicine to prepare a "profile" which consists of the values of N variables. For each such variable, the profile presents the values of a test subject and a range of values considered "normal" for each individual substance. The range of values for one substance does not depend on the range of "normal" values for another substance. A physician looks at the results and determines what substances (values) are within or outside the "normal" ranges. Thus, a certain number of variables are "normal" and the rest are "abnormal". In this invention, the "normal" or "abnormal" ranges are defined by considering simultaneously two or more substances.

While the invention has been explained by detailed description of certain specific embodiments of it, these should not be construed as limitations of the scope of the invention, but rather as an exemplification of one preferred embodiment thereof. It is understood that various substitutions and modifications can be made in it within the scope of the following claims which are intended also to cover equivalents of the disclosed best mode embodiment. Although alternative embodiments were also described above, other embodiments, therefore, may be readily devised by those skilled in the art which will embody the principles of the invention and fall within the spirit and scope thereof. Accordingly, the scope of the invention should be determined not by the embodiments illustrated, but by the enclosed claims and their legal equivalents.

What is claimed is:

1. A method of characterizing an abnormality of lipid or fatty acid biochemistry or metabolism in a human test subject by analyzing substances in a body tissue of said test subject and calculating indices derived from the quantity of each substance thus obtained, said method comprising the steps of:
   (a) obtaining at least one tissue sample from a test subject;
   (b) separating and quantifying at least two individual substances in said tissue sample(s) of said test subject to obtain the variables concentration and/or percent of each substance, including the calculation of percents of one substance as a percent of the total amount of substances within a specified group of similar substances;
   (c) defining new variables as functions of the concentration and/or percents of said substances, including formulas that depend on the arithmetic operations of addition, substraction, division and multiplication, wherein one of the variables is a concentration of one of the substances and another of the variables is a percent of a substance or ratio of concentrations of substances;
   (d) calculating indices of the biochemical status of said test subject, and p1 (e) representing the relationships among two or more of said indices into a characteristic pattern, including a point in multidimensional space called the characteristic index, or equivalent representations in the form of tables.

2. The invention of claim 1 further comprising the steps of:
   (f) forming domains which consist of sets of characteristic patterns of healthy and diseased subjects, including sets of multidimensional points in said spaces, whereby said domains are used for comparing said test subject characteristic index with similar data for healthy and diseased subjects to determine the nature of the biochemical alteration in said test subject;
   (g) storing said domains on machine-readable format;
   (h) selecting one or more domains from the group consisting of domains calculated below in (i) and (ii) and (iii):
      whereby (i) is a procedure to form domains of subjects comprising the steps of: (1) obtaining at least one tissue sample from a group of healthy subjects, (2) obtaining at least one tissue sample from one or more groups of subjects, each said group of subjects having a specific or similar disease type or biochemical abnormality, (3) for each said subjects, separating and quantifying the same substances for all subjects, at least two substances in each subject, defining new variables and calculating indices, representing those indices into patterns, storing those indices, and performing other operations in the same manner as steps (a) through (f); and (4) forming domains as sets of patterns, each domain comprising of the characteristic patterns of all subjects within said specific group of healthy subjects or said subjects with specific disease types, whereby different domains for subjects with different sociodemographic or clinical characteristics provides a multidimensional domain in which disease and normal conditions may be ascertained, including domains formed from multidimensional points or characteristic indices;

whereby (ii) is a procedure to calculate the domain of individuals with hypothesized diseases or alterations in biochemical pathways comprising the steps of: creating hypothetical or theoretical or presumed models of biochemical pathways or alterations on those pathways or diseases including enzyme blocks, calculating the characteristic patterns of individuals with said hypothetical models or alterations or diseases, and forming the domains as sets of said characteristic patterns; and whereby (iii) is any user specified domain, including those formed by modification of existing data bases of disease and healthy domains; and (i) calculating the probability that said test subject has diseases by comparing the characteristic pattern of said test subject with one or more of the said domains, including a determination of which domain is closest, or which set of points among the disease or healthy subject's points are most similar, to said test subject multidimensional point, including measuring the distances from said test subject characteristic point to each said domain selected in the previous step.

3. The invention of claim 2, further comprising:
(j) the step of calculating measures of similarities between said test subject characteristic pattern and said domains, and using said measures of similarity to calculate the probability that said test subject is healthy or has a specific disease; including measures of the distance between the domains, and said test subject and each domain; whereby the measures of similarities are calculated from formulas that combine any of the values of any number of variables using any number of combinations of the arithmetic operations of addition, substraction, multiplication and division.

4. The invention of claim 3 further comprising:
(k) preparing a mixture of nutrients containing at least two different types of fatty acids which is fed to a test subject for a user-determined period, wherein at least one of the nutrients used are either w3 or w6 fatty acids or nutrients containing said fatty acids;
(l) retesting or diagnosing again said test subject to produce a new diagnosis, including a characteristic pattern whereby the probability of each diagnosis is updated;
(m) calculating a revised disease probability;
(n) comparing said revised disease probability with said original disease probability to verify a diagnosis; and
(o) formulating said test mixture where the amounts are calculated from the measures of similarity and difference between said test subject characteristic pattern and said healthy domain.

5. The invention of claim 3 further comprising:
(k) comparing said characteristic pattern for said test subject with said domains, and determining which variables should be modified so that said test subject is judged more similar to said healthy than said disease subjects, including the identification of which variables should be modified so that the points of said test subject on each axis fall closer to the range of the healthy individuals; and
(l) transforming said variables into the specific nutrients that they refer to and into a specific nutritional mixture for said test subject, whereby said subject's health may be improved, including the preparation of a treatment nutritional mixture composed of specific nutrients to be provided to said test subject using a previously prepared data base that relates the multidimensional variables to specific nutrients; wherein said treatment mixture contains at least one w3 or w6 fatty acids or substances containing said fatty acids in proportion to the difference between said test subject characteristic pattern and said healthy domain.

6. The invention of claim 5 wherein:
said treatment mixture contains at least one w3 and one w6 fatty acids or substances containing said fatty acids in proportion to the difference between said test subject characteristic pattern and said healthy domain.

7. The invention of claim 2 wherein:
the domains exclude domains shaped like a rectangular box in n-dimensions or a rectangle in two-dimensions of euclidean geometry.

8. The invention of claim 7, further comprising:
(j) the step of calculating measures of similarities between said test subject characteristic pattern and said domains, and using said measures of similarity to calculate the probability that said test subject is healthy or has a specific disease; including measures of the distance between the domains, and said test subject and each domain; whereby the measures of similarities are calculated from formulas that combine any of the values of any number of variables using any number of combinations of the arithmetic operations of addition, substraction, multiplication and division.

9. The invention of claim 8 further comprising:
(k) preparing a mixture of nutrients containing at least two different types of fatty acids which is fed to a test subject for a user-determined period, wherein at least one of the nutrients used are either w3 or w6 fatty acids or nutrients containing said fatty acids;
(l) retesting or diagnosing again said test subject to produce a new diagnosis, including a characteristic pattern whereby the probability of each diagnosis is updated;
(m) calculating a revised disease probability;
(n) comparing said revised disease probability with said original disease probability to verify a diagnosis; and
(o) formulating said test mixture where the amounts are calculated from the measures of similarity and difference between said test subject characteristic pattern and said healthy domain.

10. The invention of claim 8 further comprising:
(k) comparing said characteristic pattern for said test subject with said domains, and determining which variables should be modified so that said test subject is judged more similar to said healthy than said disease subjects, including the identification of which variables should be modified so that the points of said test subject on each axis fall closer to the range of the healthy individuals; and (l) transforming said variables into the specific nutrients that they refer to and into a specific nutritional mixture for said test subject, whereby said subject's health may be improved, including the preparation of a treatment nutritional mixture composed of specific nutrients to be provided to said test subject using a previously prepared data base that relates the multidimensional variables to specific nutrients;

wherein said treatment mixture contains at least one w3 or w6 fatty acids or substances containing said fatty acids in proportion to the difference between said test subject characteristic pattern and said healthy domain.

11. The invention of claim 10 wherein:
said treatment mixture contains at least one w3 and one w6 fatty acids or substances containing said fatty acids in proportion to the difference between said test subject characteristic pattern and said healthy domain.

12. A method of characterizing an abnormality of lipid or fatty acid biochemistry or metabolism in a human test subject by analyzing substances in a body tissue of said test subject and calculating indices derived from the quantity of each substance thus obtained, said method comprising the steps of:

(a) obtaining at least one tissue sample from a test subject;

(b) separating and quantifying at least two individual substances in said tissue sample(s) of said test subject to obtain the variables concentration and/or percent of each substance, including the calculation of percents of one substance as a percent of the total amount of substances within a specified group of similar substances;

(c) defining new variables as functions of the concentration and/or percents of said substances, including formulas that depend on the arithmetic operations of addition, substraction, division and multiplication, wherein one of the variables is a concentration of one of the substances and another of the variables is also a concentration of one of the substances and said substances are selected from the group consisting of lipids and fatty acids or their derivatives, including fatty acids in specific lipids, and the remaining variables may be obtained from any substance;

(d) calculating indices of the biochemical status of said test subject, said indices being the specific values of said variables for said test subject; and (e) representing the relationships among two or more of said indices into a characteristic pattern, including a point in multidimensional space called the characteristic index, or equivalent representations in the form of tables.

13. The invention of claim 12 further comprising the steps of:

(f) forming domains which consist of sets of characteristic patterns of healthy and diseased subjects, including sets of multidimensional points in said spaces, whereby said domains are used for comparing said test subject characteristic index with similar data for healthy and diseased subjects to determine the nature of the biochemical alteration in said test subject;

(g) storing said domains on machine-readable format;

(h) selecting one or more domains from the group consisting of domains calculated below in (i) and (ii) and (iii):

whereby (i) is a procedure to form domains of subjects comprising the steps of: (1) obtaining at least one tissue sample from a group of healthy subjects, (2) obtaining at least one tissue sample from one or more groups of subjects, each said group of subjects having a specific or similar disease type or biochemical abnormality, (3) for each said subjects, separating and quantifying the same substances for all subjects, at least two substances in each subject, defining new variables and calculating indices, representing those indices into patterns, storing those indices, and performing other operations in the same manner as steps (a) through (f); and (4) forming domains as sets of patterns, each domain comprising of the characteristic patterns of all subjects within said specific group of healthy subjects or said subjects with specific disease types, whereby different domains for subjects with different sociodemographic or clinical characteristics provides a multidimensional domain in which disease and normal conditions may be ascertained, including domains formed from multidimensional points or characteristic indices;

whereby (ii) is a procedure to calculate the domain of individuals with hypothesized diseases or alterations in biochemical pathways comprising the steps of: creating hypothetical or theoretical or presumed models of biochemical pathways or alterations on those pathways or diseases including enzyme blocks, calculating the characteristic patterns of individuals with said hypothetical models or alterations or diseases, and forming the domains as sets of said characteristic patterns; and whereby (iii) is any user specified domain, including those formed by modification of existing data bases of disease and healthy domains; and (i) calculating the probability that said test subject has diseases by comparing the characteristic pattern of said test subject with one or more of the said domains, including a determination of which domain is closest, or which set of points among the disease or healthy subject's points are most similar, to said test subject multidimensional point, including measuring the distances from said test subject characteristic point to each said domain selected in the previous step.

14. The invention of claim 13, further comprising:

(j) the step of calculating measures of similarities between said test subject characteristic pattern and said domains, and using said measures of similarity to calculate the probability that said test subject is healthy or has a specific disease; including measures of the distance between the domains, and said test subject and each domain; whereby the measures of similarities are calculated from formulas that combine any of the values of any number of variables using any number of combinations of the arithmetic operations of addition, substraction, multiplication and division.

15. The invention of claim 14 further comprising:

(k) preparing a mixture of nutrients containing at least two different types of fatty acids which is fed to a test subject for a user-determined period, wherein at least one of the nutrients used are either w3 or w6 fatty acids or nutrients containing said fatty acids;

(l) retesting or diagnosing again said test subject to produce a new diagnosis, including a characteristic pattern whereby the probability of each diagnosis is updated;

(m) calculating a revised disease probability;

(n) comparing said revised disease probability with said original disease probability to verify a diagnosis; and (o) formulating said test mixture where the amounts are calculated from the measures of similarity and difference between said test subject characteristic pattern and said healthy domain.

16. The invention of claim 14 further comprising:

(k) comparing said characteristic pattern for said test subject with said domains, and determining which variables should be modified so that said test subject is judged more similar to said healthy than said disease subjects, including the identification of which variables should be modified so that the points of said test subject on each axis fall closer to the range of the healthy individuals; and (l) transforming said variables into the specific nutrients that they refer to and into a specific nutritional mixture for said test subject, whereby said subject's health may be improved, including the preparation of a treatment nutritional mixture composed of specific nutrients to be provided to said test subject using a previously prepared data base that relates the multidimensional variables to specific nutrients; wherein said treatment mixture contains at least one w3 or w6 fatty acids or substances containing said fatty acids in proportion to the difference between said test subject characteristic pattern and said healthy domain.

17. The invention of claim 16 wherein:

said treatment mixture contains at least one w3 and one w6 fatty acids or substances containing said fatty acids in proportion to the difference between said test subject characteristic pattern and said healthy domain.

18. The invention of claim 13 wherein:

the domains exclude domains shaped like a rectangular box in n-dimensions or a rectangle in two-dimensions of euclidean geometry.

19. The invention of claim 18, further comprising:

(j) the step of calculating measures of similarities between said test subject characteristic pattern and said domains, and using said measures of similarity to calculate the probability that said test subject is healthy or has a specific disease; including measures of the distance between the domains, and said test subject and each domain; whereby the measures of similarities are calculated from formulas that combine any of the values of any number of variables using any number of combinations of the arithmetic operations of addition, substraction, multiplication and division.

20. The invention of claim 19 further comprising:

(k) preparing a mixture of nutrients containing at least two different types of fatty acids which is fed to a test subject for a user-determined period, wherein at least one of the nutrients used are either w3 or w6 fatty acids or nutrients containing said fatty acids;

(l) retesting or diagnosing again said test subject to produce a new diagnosis, including a characteristic pattern whereby the probability of each diagnosis is updated;

(m) calculating a revised disease probability;

(o) comparing said revised disease probability with said original disease probability to verify a diagnosis; and formulating said test mixture where the amounts are calculated from the measures of similarity and difference between said test subject characteristic pattern and said healthy domain.

21. The invention of claim 19 further comprising:

(k) comparing said characteristic pattern for said test subject with said domains, and determining which variables should be modified so that said test subject is judged more similar to said healthy than said disease subjects, including the identification of which variables should be modified so that the points of said test subject on each axis fall closer to the range of the healthy individuals; and (l) transforming said variables into the specific nutrients that they refer to and into a specific nutritional mixture for said test subject, whereby said subject's health may be improved, including the preparation of a treatment nutritional mixture composed of specific nutrients to be provided to said test subject using a previously prepared data base that relates the multidimensional variables to specific nutrients; wherein said treatment mixture contains at least one w3 or w6 fatty acids or substances containing said fatty acids in proportion to the difference between said test subject characteristic pattern and said healthy domain.

22. The invention of claim 21 wherein:

said treatment mixture contains at least one w3 and one w6 fatty acids or substances containing said fatty acids in proportion to the difference between said test subject characteristic pattern and said healthy domain.

23. A method of characterizing an abnormality of lipid or fatty acid biochemistry or metabolism in a human test subject by analyzing substances in a body tissue of said test subject and calculating indices derived from the quantity of each substance thus obtained, said method comprising the steps of:

(a) obtaining at least one tissue sample from a test subject;

(b) separating and quantifying at least two individual substances in said tissue sample(s) of said test subject to obtain the variables concentration and/or percent of each substance, including the calculation of percents of one substance as a percent of the total amount of substances within a specified group of similar substances;

(c) defining new variables as functions of the concentration and/or percents of said substances, including formulas that depend on the arithmetic operations of addition, substraction, division and multiplication, wherein one of the variables is a percent of a substance or ratio of concentrations of substances and another of the variables is also a percent of a substance or ratio of concentrations of substances and said substances are selected from the group consisting of lipids and fatty acids or their derivatives, including fatty acids in specific lipids, and the remaining variables may be obtained from any substance;

(d) calculating indices of the biochemical status of said test subject, said indices being the specific values of said variables for said test subject; and (e) representing the relationships among two or more of said indices into a characteristic pattern, including a point in multidimensional space called the characteristic index, or equivalent representations in the form of tables.

24. The invention of claim 23 further comprising the steps of:
(f) forming domains which consist of sets of characteristic patterns of healthy and diseased subjects, including sets of multidimensional points in said spaces, whereby said domains are used for comparing said test subject characteristic index with similar data for healthy and diseased subjects to determined the nature of the biochemical alteration in said test subject;
(g) storing said domains on machine-readable format;
(h) selecting one or more domains from the group consisting of domains calculated below in (i) and (ii) and (iii):
whereby (i) is a procedure to form domains of subjects comprising the steps of: (1) obtaining at least one tissue sample from a group of healthy subjects, (2) obtaining at least one tissue sample from one or more groups of subjects, each said group of subjects having a specific or similar disease type or biochemical abnormality, (3) for each said subjects, separating and quantifying the same substances for all subjects, at least two substances in each subject, defining new variables and calculating indices, representing those indices into patterns, storing those indices, and performing other operations in the same manner as steps (a) through (f); and (4) forming domains as set of patterns, each domain comprising of the characteristic patterns of all subjects within said specific group of healthy subjects or said subjects with specific disease types, whereby different domains for subjects with different sociodemographic or clinical characteristics provides a multidimensional domain in which disease and normal conditions may be ascertained, including domains formed from multidimensional points or characteristic indices;
whereby (ii) is a procedure to calculate the domain of individuals with hypothesized diseases or alterations in biochemical pathways comprising the steps of: creating hypothetical or theoretical or presumed models of biochemical pathways or alterations on those pathways or diseases including enzyme blocks, calculating the characteristic patterns of individuals with said hypothetical models or alterations or diseases, and forming the domains as sets of said characteristic patterns; and
whereby (iii) is any user specified domain, including those formed by modification of existing data bases of disease and healthy domains; and
(i) calculating the probability that said test subject has diseases by comparing the characteristic pattern of said test subject with one or more of the said domains, including a determination of which domain is closest, or which set of points among the disease or healthy subject's points are most similar, to said test subject multidimensional point, including measuring the distances from said test subject characteristic point to each said domain selected in the previous step.

25. The invention of claim 24, further comprising:

(j) the step of calculating measures of similarities between said test subject characteristic pattern and said domains, and using said measures of similarity to calculate the probability that said test subject is healthy or has a specific disease; including measures of the distance between the domains, and said test subject and each domain; whereby the measures of similarities are calculated from formulas that combine any of the values of any number of variables using any number of combinations of the arithmetic operations of addition, substraction, multiplication and division.

26. The invention of claim 25 further comprising:
(k) preparing a mixture of nutrients containing at least two different types of fatty acids which is fed to a test subject for a user-determined period, wherein at least one of the nutrients used are either w3 or w6 fatty acids or nutrients containing said fatty acids;
(l) retesting or diagnosing again said test subject to produce a new diagnosis, including a characteristic pattern whereby the probability of each diagnosis is updated;
(m) calculating a revised disease probability;
(n) comparing said revised disease probability with said original disease probability to verify a diagnosis; and
(o) formulating said test mixture where the amounts are calculated from the measures of similarity and difference between said test subject characteristic pattern and said healthy domain.

27. The invention of claim 25 further comprising:
(k) comparing said characteristic pattern for said test subject with said domains, and determining which variables should be modified so that said test subject is judged more similar to said healthy than said disease subjects, including the identification of which variables should be modified so that the points of said test subject on each axis fall closer to the range of the healthy individuals; and
(l) transforming said variables into the specific nutrients that they refer to and into a specific nutritional mixture for said test subject, whereby said subject's health may be improved, including the preparation of a treatment nutritional mixture composed of specific nutrients to be provided to said test subject using a previously prepared data base that relates the multidimensional variables to specific nutrients; wherein said treatment mixture contains at least one w3 or w6 fatty acids or substances containing said fatty acids in proportion to the difference between said test subject characteristic pattern and said healthy domain.

28. The invention of claim 27 wherein:
said treatment mixture contains at least one w3 and one w6 fatty acids or substances containing said fatty acids in proportion to the difference between said test subject characteristic pattern and said healthy domain.

29. The invention of claim 24 wherein:
the domains exclude domains shaped like a rectangular box in n-dimensions or a rectangle in two-dimensions of euclidean geometry.

30. The invention of claim 29, further comprising:
(j) the step of calculating measures of similarities between said test subject characteristic pattern and said domains, and using said measures of similarity to calculate the probability that said test subject is healthy or has a specific disease; including measures of the distance between the domains, and said test subject and each domain; whereby the measures of similarities are calculated from formulas that combine any of the values of any number of variables using any number of combinations of the arithmetic operations of addition, substraction, multiplication and division.

31. The invention of claim 30 further comprising:
(k) preparing a mixture of nutrients containing at least two different types of fatty acids which is fed to a test subject for a user-determined period, wherein at least one of the nutrients used are either w3 or w6 fatty acids or nutrients containing said fatty acids;
(l) retesting or diagnosing again said test subject to produce a new diagnosis, including a characteristic pattern whereby the probability of each diagnosis is updated;
(m) calculating a revised disease probability;
(n) comparing said revised disease probability with said original disease probability to verify a diagnosis; and
(o) formulating said test mixture where the amounts are calculated from the measures of similarity and difference between said test subject characteristic pattern and said healthy domain.

32. The invention of claim 30 further comprising:
(k) comparing said characteristic pattern for said test subject with said domains, and determining which variables should be modified so that said test subject is judged more similar to said healthy than said disease subjects, including the identification of which variables should be modified so that the points of said test subject on each axis fall closer to the range of the healthy individuals; and
(l) transforming said variables into the specific nutrients that they refer to and into a specific nutritional mixture for said test subject, whereby said subject's health may be improved, including the preparation of a treatment nutritional mixture composed of specific nutrients to be provided to said test subject using a previously prepared data base that relates the multidimensional variables to specific nutrients; wherein said treatment mixture contains at least one w3 or w6 fatty acids or substances containing said fatty acids in proportion to the difference between said test subject characteristic pattern and said healthy domain.

33. The invention of claim 32 wherein:
said treatment mixture contains at least one w3 and one w6 fatty acids or substances containing said fatty acids in proportion to the difference between said test subject characteristic pattern and said healthy domain.

34. A disease diagnostic method comprising the steps of:
(a) characterizing an abnormality of lipid or fatty acid biochemistry or metabolism of a test subject with a diagnostic method, which method includes examination of at least one substance from at least one test subject tissue sample and comparing said substance with those of a group of healthy subjects, wherein at least one of the substances examined is from a group consisting of an w3 or an w6 fatty acid or a substance containing said fatty acid or a fatty acid found in human plasma in concentrations below 2 mg/dl;
(b) preparing a mixture of nutrients which is fed to a test subject for a user-determined period, wherein one of the nutrients used contains no less than 5 grams nor more than 90 grams of a fatty acid selected from one of the following classes below in (i) through (iv) and the amount of calories from this fatty acid is over 20% of the total calories in the test mixture: (i) an w3 fatty acid or linolenic acid or a derivative of linolenic acid, (ii) an w6 fatty acid or linoleic acid or a derivative of linoleic acid, (iii) a fatty acid found in human plasma in concentrations below 2 mg/dl, or (iv) a nutrient containing one of the fatty acids in (i), or (ii) or (iii);
(c) retesting or diagnosing again said test subject to produce a new diagnosis, including a characteristic pattern whereby the probability of each diagnosis is updated;
(d) calculating a revised disease probability;
(e) comparing said revised disease probability with said original disease probability to verify a diagnosis.

35. The invention of claim 34, wherein said test mixture consists of one of the following classes:
(a) a mixture containing both w3 and w6 fatty acids or substances containing said fatty acids and the ratio of w6 to w3 fatty acids is in the range 0.5:9 to 12:1.

36. The invention of claim 34, wherein:
said test mixture contains both w3 and w6 fatty acids or substances containing said fatty acids and the ratio of w6 to w3 fatty acids is in the range 0.5:9 to 12:1; and
the amounts of w3 and w6 fatty acids in said test mixture are calculated from the measures of similarity and difference between said test subject characteristic pattern and said healthy subjects.

37. A method of diagnosing and detecting biochemical abnormalities of lipids and fatty acids in a human subject, which method comprises the steps of:
obtaining at least one tissue sample from each subject of a group of healthy subjects;
obtaining at least one tissue sample from each subject of a plurality of groups of subjects, each group of subjects having a specific disease type or biochemical abnormality;
separating and quantifying at least two substances in each tissue sample to obtain a concentration and/or percentage of each substance therein;
defining variables as functions of the concentration and/or percentage of each individual substance;
calculating from the quantities of each substance the values for said variables wherein one of the variables is a concentration of one of the substances and another of the variables is a percent of a substance or ratio of concentrations of substances;
forming a multidimensional space using two or more of said variables as coordinates;
representing the relationships among the values of the variables by producing one multidimensional point for each subject;
plotting multidimensional domains in said multidimensional space wherein each domain represents the multidimensional points for all subjects within an individual group;
obtaining a test tissue sample from a test subject;
separating and quantifying at least two substances in said test sample to obtain a concentration and/or percentage of each individual substance therein;
calculating from the quantities of each substance the values for said variables, wherein one of the variables is a concentration of one of the substances and another of the variables is a percent of a substance or ratio of concentrations of substances;

producing a multidimensional point for said test subject in terms of said coordinate variables;

plotting said test subject multidimensional point in said multidimensional space;

measuring the distances from said test subject multidimensional point to each said domain; and calculating a first disease probability for said test subject for each said domain based on the proximity of said test subject multidimensional point to each disease domain.

38. The invention of claim 37 further comprising:

calculating a test or treatment nutritional mixture containing fatty acids in proportion to the difference between said test subject multidimensional point and said healthy domain to reduce said disease probability, wherein at least one of the fatty acids is no less than 5 grams nor more than 90 grams either an w3 or w6 fatty acid and the amount of calories from this fatty acid is over 20% of the total calories in the test mixture;

administering said nutritional mixture to said test subject;

retesting said test subject to produce a new multidimensional point;

calculating a new disease probability; and comparing said second disease probability with said first disease probability to verify a diagnosis or improvement in healthy status.

39. The invention of claim 38, wherein:

said test nutritional mixture contains both w3 and w6 fatty acids or substances containing said fatty acids.

40. A method of diagnosing and detecting biochemical abnormalities of lipids and fatty acids in a human subject, which method comprises the steps of:

obtaining at least one tissue sample from each subject of a group of healthy subjects;

obtaining at least one tissue sample from each subject of a plurality of groups of subjects, each group of subjects having a specific disease type or biochemical abnormality;

separating and quantifying at least two substances in each tissue sample to obtain a concentration and/or percentage of each substance therein;

defining variables as functions of the concentration and/or percentage of each individual substance;

calculating from the quantities of each substance the values for said variables wherein one of the variables is a concentration of one of the substances and another of the variables is also a concentration of one of the substances and said substances are selected from the group consisting of lipids and fatty acids or their derivatives, including fatty acids in specific lipids, and the remaining variables may be obtained from any substance;

forming a multidimensional space using two or more of said variables as coordinates;

representing the relationships among the values of the variables by producing one multidimensional point for each subject;

plotting multidimensional domains in said multidimensional space wherein each domain represents the multidimensional points for all subjects within an individual group;

obtaining a test tissue sample from a test subject;

separating and quantifying at least two substances in said test sample to obtain a concentration and/or percentage of each individual substance therein;

calculating from the quantities of each substance the values for said variables wherein one of the variables is a concentration of one of the substances and another of the variables is also a concentration of one of the substances and said substances are selected from the group consisting of lipids and fatty acids or their derivatives, including fatty acids in specific lipids, and the remaining variables may be obtained from any substance;

producing a multidimensional point for said test subject in terms of said coordinate variables;

plotting said test subject multidimensional point in said multidimensional space;

measuring the distances from said test subject multidimensional point to each said domain; and calculating a first disease probability for said test subject for each said domain based on the proximity of said test subject multidimensional point to each disease domain.

41. The invention of claim 40 further comprising:

calculating a test or treatment nutritional mixture containing fatty acids in proportion to the difference between said test subject multidimensional point and said healthy domain to reduce said disease probability, wherein at least one of the fatty acids is no less than 5 grams nor more than 90 grams grams of either an w3 or w6 fatty acid and the amount of calories from this fatty acid is over 20% of the total calories in the test mixture;

administering said nutritional mixture to said test subject;

retesting said test subject to produce a new multidimensional point;

calculating a new disease probability; and comparing said second disease probability with said first disease probability to verify a diagnosis or improvement in health status.

42. The invention of claim 41, wherein:

said test nutritional mixture contains both w3 and w6 fatty acids or substances containing said fatty acids.

43. A method of diagnosing and detecting biochemical abnormalities of lipids and fatty acids in a human subject, which method comprises the steps of:

obtaining at least one tissue sample from each subject of a group of healthy subjects;

obtaining at least one tissue sample from each subject of a plurality of groups of subjects, each group of subjects having a specific disease type or biochemical abnormality;

separating and quantifying at least two substances in each tissue sample to obtain a concentration and/or percentage of each substance therein wherein one of the variables is a percent of a substance or ratio of concentrations of substances and another of the variables is also a percent of a substance or ratio of concentrations of substances and said substances are selected from the group consisting of lipids and fatty acids or their derivatives, including fatty acids in specific lipids, and the remaining variables may be obtained from any substance;

defining variables as functions of the concentration and/or percentage of each individual substance;

calculating from the quantities of each substance the values for said variables;

forming a multidimensional space using two or more of said variables as coordinates;

representing the relationships among the values of the variables by producing one multidimensional point for each subject;

plotting multidimensional domains in said multidimensional space wherein each domain represents the multidimensional points for all subjects within an individual group;

obtaining a test tissue sample from a test subject;

separating and quantifying at least two substances in said test sample to obtain a concentration and/or percentage of each individual substance therein;

calculating from the quantities of each substance the values for said variables wherein one of the variables is a percent of a substance or ratio of concentrations of substances and another of the variables is also a percent of a substance or ratio of concentrations of substances and said substances are selected from the group consisting of lipids and fatty acids or their derivatives, including fatty acids in specific lipids, and the remaining variables may be obtained from any substance;

producing a multidimensional point for said test subject in terms of said coordinate variables;

plotting said test subject multidimensional point in said multidimensional space;

measuring the distances from said test subject multidimensional point to each said domain; and calculating a first disease probability for said test subject for each said domain based on the proximity of said test subject multidimensional point of each disease domain.

44. The invention of claim 43 further comprising:

calculating a test or treatment nutritional mixture containing fatty acids in proportion to the difference between said test subject multidimensional point and said healthy domain to reduce said disease probability, wherein at least one of the fatty acids is no less than 5 grams nor more than 90 grams of either an w3 or w6 fatty acid and the amount of calories from this fatty acid is over 20% of the total calories in the test mixture;

administering said nutritional mixture to said test subject:

retesting said test subject to produce a new multidimensional point;

calculating a new disease probability; and comparing said second disease probability with said first disease probability to verify a diagnosis or improvement in health status.

45. The invention of claim 44, wherein:
said test nutritional mixture contains both w3 and w6 fatty acids or substances containing said fatty acids.

46. The invention of claim 1 wherein:
said substances are selected from the group consisting of lipids and fatty acids or their derivatives, including fatty acids in specific lipids, and the remaining variables may be obtained from any substance.

47. The invention of claim 2 wherein:
said substances are selected from the group consisting of lipids and fatty acids or their derivatives, including fatty acids in specific lipids, and the remaining variables may be obtained from any substance.

48. The invention of claim 3 wherein:
said substances are selected from the group consisting of lipids and fatty acids or their derivatives, including fatty acids in specific lipids, and the remaining variables may be obtained from any substance.

49. The invention of claim 4 wherein:
said substances are selected from the group consisting of lipids and fatty acids or their derivatives, including fatty acids in specific lipids, and the remaining variables may be obtained from any substance.

50. The invention of claim 5 wherein:
said substances are selected from the group consisting of lipids and fatty acids or their derivatives, including fatty acids in specific lipids, and the remaining variables may be obtained from any substance.

51. The invention of claim 7 wherein:
said substances are selected from the group consisting of lipids and fatty acids or their derivatives, including fatty acids in specific lipids, and the remaining variables may be obtained from any substance.

52. The invention of claim 8 wherein:
said substances are selected from the group consisting of lipids and fatty acids or their derivatives, including fatty acids in specific lipids, and the remaining variables may be obtained from any substance.

53. The invention of claim 9 wherein:
said substances are selected from the group consisting of lipids and fatty acids or their derivatives, including fatty acids in specific lipids, and the remaining variables may be obtained from any substance.

54. The invention of claim 10 wherein:
said substances are selected from the group consisting of lipids and fatty acids or their derivatives, including fatty acids in specific lipids, and the remaining variables may be obtained from any substance.

55. The invention of claim 37 wherein:
said substances are selected from the group consisting of lipids and fatty acids or their derivatives, including fatty acids in specific lipids, and the remaining variables may be obtained from any substance.

* * * * *